(12) United States Patent
Sako et al.

(10) Patent No.: US 7,558,440 B2
(45) Date of Patent: Jul. 7, 2009

(54) IMAGE PROCESSING APPARATUS AND METHOD, PHOTOGRAPHING SYSTEM, CONTROLLING METHOD FOR THE SYSTEM, AND COMPUTER-READABLE MEMORY

(75) Inventors: Tsukasa Sako, Utsunomiya (JP);
Takahiro Oshino, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 449 days.

(21) Appl. No.: 11/445,335

(22) Filed: Jun. 2, 2006

(65) Prior Publication Data
US 2006/0222229 A1 Oct. 5, 2006

Related U.S. Application Data

(62) Division of application No. 09/408,447, filed on Sep. 29, 1999, now abandoned.

(30) Foreign Application Priority Data

Sep. 30, 1998 (JP) ................................. 10-278729
Sep. 30, 1998 (JP) ................................. 10-279167

(51) Int. Cl.
G06K 9/00 (2006.01)
G06K 9/32 (2006.01)
H04N 1/10 (2006.01)
H04N 1/393 (2006.01)

(52) U.S. Cl. ....................... 382/298; 382/132; 358/449; 358/451

(58) Field of Classification Search .................. None
See application file for complete search history.

(56) References Cited

U.S. PATENT DOCUMENTS 5,042,060 A 8/1991 Sakakihara ................ 378/172
5,432,532 A 7/1995 Mochimaru et al. ......... 347/176
5,644,611 A 7/1997 McShane et al. ............ 128/922
5,663,809 A * 9/1997 Miyaza et al. .............. 358/450

(Continued)

FOREIGN PATENT DOCUMENTS

JP 6-115208 4/1994

(Continued)

OTHER PUBLICATIONS

Hasegawa, Toriwaki, and Fukumura, "Software System AISCR-V3 for Automatically Screening of Chest Photofluorograms", IECE Transactions J66-D10, (1983), together with English-language abstract.

Primary Examiner—Charles Kim
(74) Attorney, Agent, or Firm—Fitzpatrick, Cella, Harper & Scinto

(57) ABSTRACT

This invention has as its object to provide an image processing system and a control method for the system, a photographing system and a control method for the system, and a computer-readable memory, which can efficiently photograph without any increase in X-ray dose for a person to be examined. To achieve this object, an output mode input section inputs an output mode representing the output format of an observation area as a to-be-output area in an image to an output medium. An output medium size input section inputs the size of the effective image area of the output medium. The output determination section determines the output method of the observation area on the basis of the observation area and contents input by the input sections.

15 Claims, 21 Drawing Sheets

U.S. PATENT DOCUMENTS

| | | | |
|---|---|---|---|
| 5,774,232 A | 6/1998 | Tabata et al. | 358/401 |
| 5,852,503 A | 12/1998 | Kawaoka | 358/527 |
| 6,335,795 B1 * | 1/2002 | Neuhard et al. | 358/1.15 |
| 6,335,796 B1 | 1/2002 | Endo et al. | 358/1.15 |
| 6,356,651 B2 | 3/2002 | Murakami | 128/922 |
| 6,671,394 B1 | 12/2003 | Sako | 382/132 |
| 6,714,623 B2 | 3/2004 | Sako et al. | 378/98.8 |

FOREIGN PATENT DOCUMENTS

| | | |
|---|---|---|
| JP | 6-247000 | 9/1994 |
| JP | 09-098970 | 4/1997 |
| JP | 9-297363 | 11/1997 |
| JP | 10-243020 | 9/1998 |

* cited by examiner

F I G. 13
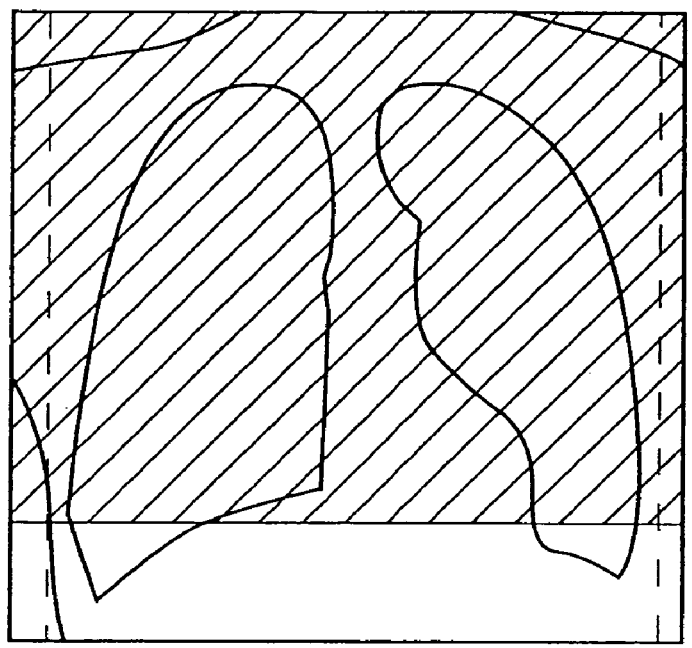
F I G. 14
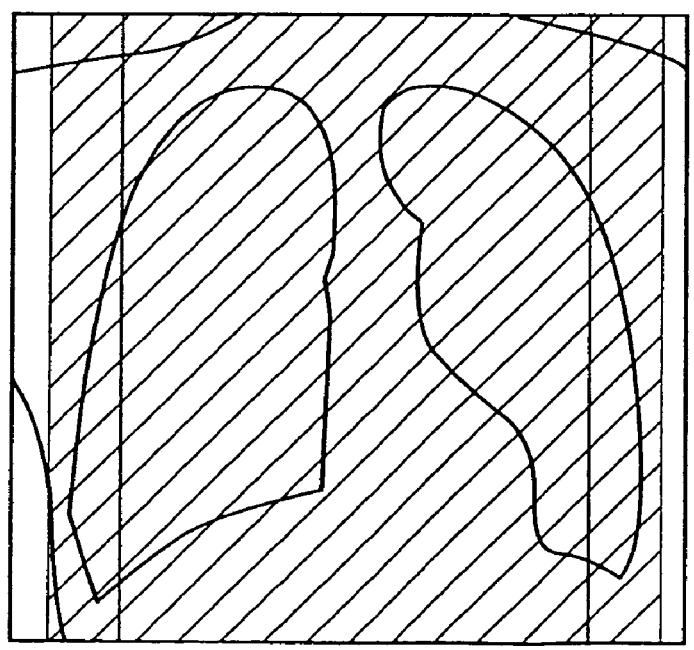

F I G. 16
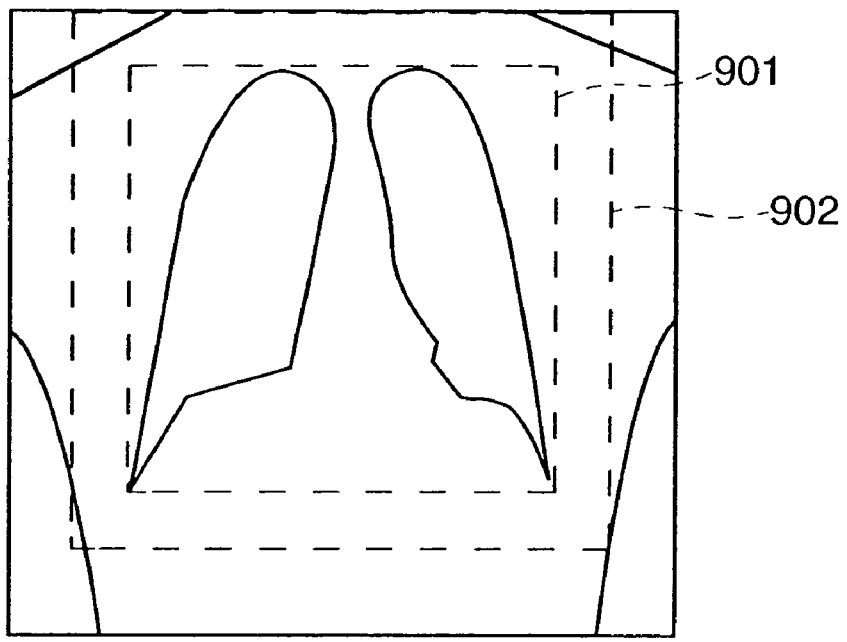
F I G. 17
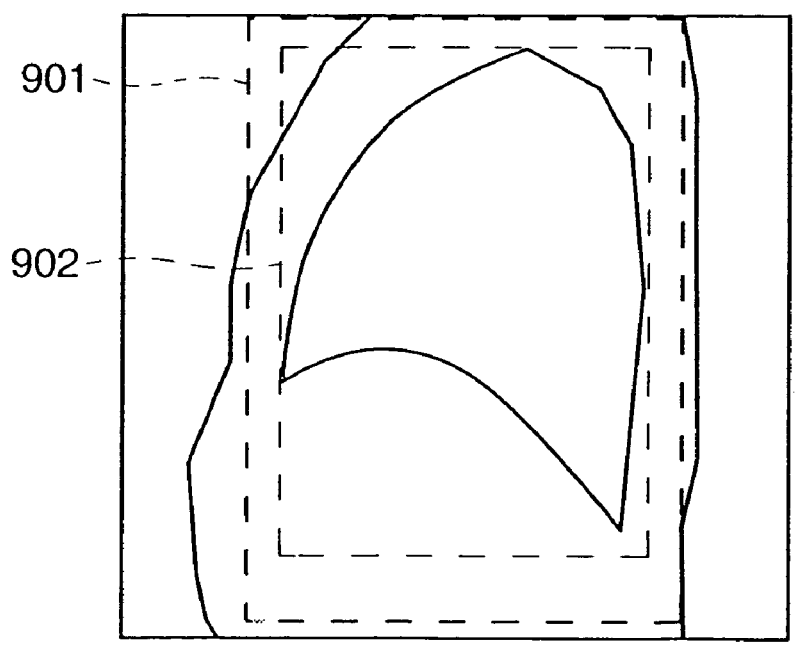

IRRADIATION FIELD RECOGNITION AREA
SENSOR AREA
FILM AREA

17inch
=43cm
=2,688PIXELS
(1PIXEL=160μm)

17inch
=43cm
=2,688PIXELS
(1PIXEL=160μm)

| INCH SIZE (cm) | NAME | LAYOUT CLASSIFICATION | THE NUMBER OF PIXELS |
|---|---|---|---|
| 14×17(35×43) | HALF-SIZE PORTRAIT | VERTICAL | 2048 2560 |
| 17×14(43×35) | HALF-SIZE LANDSCAPE | HORIZONTAL | 2560 2048 |
| 14×14(35×35) | LARGE SIZE | VERTICAL/HORIZONTAL | 2048 2048 |
| 10×12(24×30) | 1/4-SIZE PORTRAIT | VERTICAL | 1768 1450 |
| 12×10(30×24) | 1/4-SIZE LANDSCAPE | HORIZONTAL | 1450 1768 |

F I G. 27
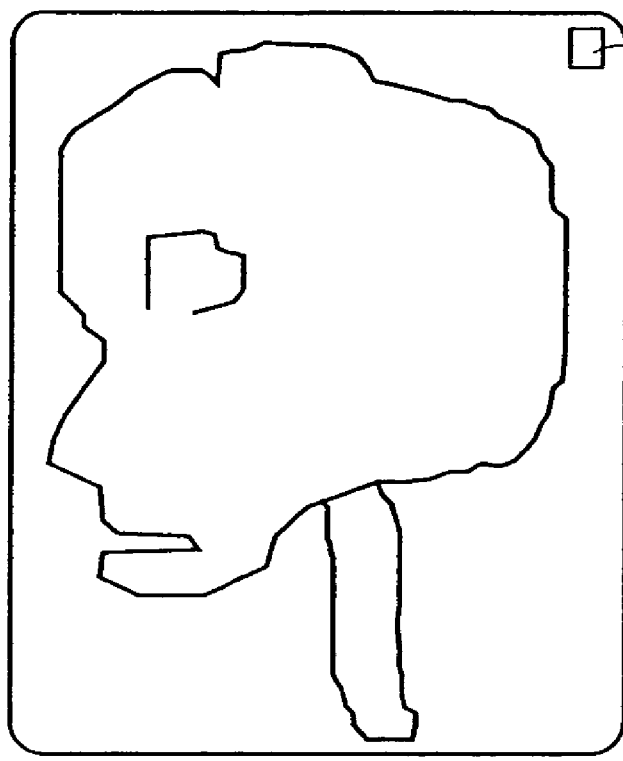
1901
REDUCTION MARKING

IMAGE PROCESSING APPARATUS AND METHOD, PHOTOGRAPHING SYSTEM, CONTROLLING METHOD FOR THE SYSTEM, AND COMPUTER-READABLE MEMORY

This application is a divisional of application Ser. No. 09/408,447, filed Sep. 29, 1999, the contents of which are incorporated by reference herein.

BACKGROUND OF THE INVENTION

1. Field of the Invention

The present invention relates to an image processing system and a control method for the system, a photographing system and a control method for the system, and a computer-readable memory, which process an image signal obtained by electronically converting an image input and output the processed signal.

2. Description of the Related Art

In a conventional scheme used to obtain a medical X-ray radiographic image for a long time, the distribution of X-rays transmitted through a human body is converted into a fluorescence distribution of a phosphor, the light intensity is directly printed on a film, and the film is developed. In recent years, a radiographic image is read out as an electrical signal using a scheme of forming a latent image of an X-ray intensity distribution as an energy on a photostimulable phosphor and reading out the image, a scheme of directly reading the fluorescence distribution of a phosphor by X-rays as an image, or a technique without use of a fluorescence distribution. The electrical signal is converted into digital data to form a digital image. Use of digital images allows efficient filing, practical use of remote diagnosis, and improvement of the diagnostic technology and efficiency. In addition, digital images make various image processing operations possible and are also changing the diagnosis method.

Under these circumstances, as disclosed in Japanese Patent Laid-Open No. 09-098970 proposed by the present applicant, an X-ray image sensing apparatus using a wide-screen two-dimensional solid-state image sensing device has been provided. An X-ray detection apparatus capable of detecting an X-ray radiographic image larger than a conventional regular size film can be manufactured.

Generally, a film used to photograph an X-ray image of a thoracic or abdominal portion has a half size (14"×17") or a large size (14"×14"). As for the direction of a film in photographing, a film with half size is generally set long in the vertical direction (so-called portrait). Sometimes, an image to be photographed does not completely fall within the film area depending on the height or form of the person to be examined. When the image to be photographed stretches out in the vertical direction, the person to be examined must vertically move to acquire a photographed image. In this case, X-rays are radiated twice to acquire a photographed image, resulting in an increase in X-ray dose for the person to be examined. When the image to be photographed stretches out in the horizontal direction, the person to be examined must move in the horizontal direction to photograph the image twice. Alternatively, a horizontally elongated film (so-called landscape) as shown in FIG. 3 is used to acquire a photographed image. When the to-be-photographed image of the person to be examined does not fall within the film area, the X-ray dose for the person to be examined increases. Additionally, the operation becomes cumbersome because, e.g., the direction of the X-ray detection apparatus need be changed from portrait to landscape.

The sensor area of a digital X-ray sensing apparatus may be larger than a film screen system. For example, the CXDI (trademark) available from Canon has a size of 17" (43 cm)× 17" (43 cm). Commercially available films have only predetermined sizes: 14"×17", 14"×14", or 10"×12". Hence, to print an image on a commercially available film, the area to be extracted from a 17"×17" image, and the film to be used must be carefully selected.

On the other hand, for many commercially available image viewers, allowable image sizes are predetermined. Especially, the maximum size is often predetermined. For commercially available diagnostic viewers, the maximum allowable size of an image is 2,048×2,048 pixels. Hence, even when an image is to be output to a medium other than a film, the same problem as for a film is posed.

SUMMARY OF THE INVENTION

The present invention has been made in consideration of the above situation, and has as its object to provide an image processing system and a control method for the system, a photographing system and a control method for the system, and a computer-readable memory, which can efficiently photograph without any increase in X-ray dose for a person to be examined.

In order to achieve the above object, according to the present invention, there is provided an image processing system for processing an image signal obtained by electronically converting an input image and outputting the image signal, comprising:

output mode input means for inputting an output mode representing an output format of an observation area as a to-be-output area in the image to an output medium;

input means for inputting a size of an effective image area of the output medium; and determination means for determining an output method of the observation area on the basis of the observation area and contents input by the output mode input means and the input means.

It is another object of the present invention to make it possible to output an image while selecting an appropriate output size from a plurality of predetermined output sizes in accordance with the to-be-output portion of the image to be output, and appropriately output the image to an existing medium or viewer without damaging the information.

In order to achieve the above object, according to the present invention, there is provided an image processing apparatus comprising:

acquisition means for specifying a to-be-output area of an image represented by image data as an output image and acquiring a size of the output image;

selection means for selecting, on the basis of the size of the output image acquired by the acquisition means, one image output size from a plurality of types of image output sizes set in advance;

layout determination means for determining a layout of the output image in an output area having the image output size selected by the selection means;

display means for displaying on the basis of a layout state determined by the layout determination means; and change means for changing the layout state of the output image in the output area in accordance with an instruction for changing the layout state displayed by the display means.

Other features and advantages of the present invention will be apparent from the following description taken in conjunc-

BRIEF DESCRIPTION OF THE DRAWINGS

FIG. 13 is a view for explaining the image switching output mode in the first embodiment of the present invention;

FIG. 14 is a view for explaining a 2-image output mode in the first embodiment of the present invention;

FIG. 16 is a view for explaining the procedure of acquiring observation area setting information in the third embodiment of the present invention;

FIG. 17 is a view for explaining the procedure of acquiring observation area setting information in the third embodiment of the present invention;

FIG. 27 is a view showing an example of reduction marking;

DETAILED DESCRIPTION OF THE PREFERRED EMBODIMENTS

The preferred embodiments of the present invention will be described below with reference to the accompanying drawings.

First Embodiment

Figure 1:
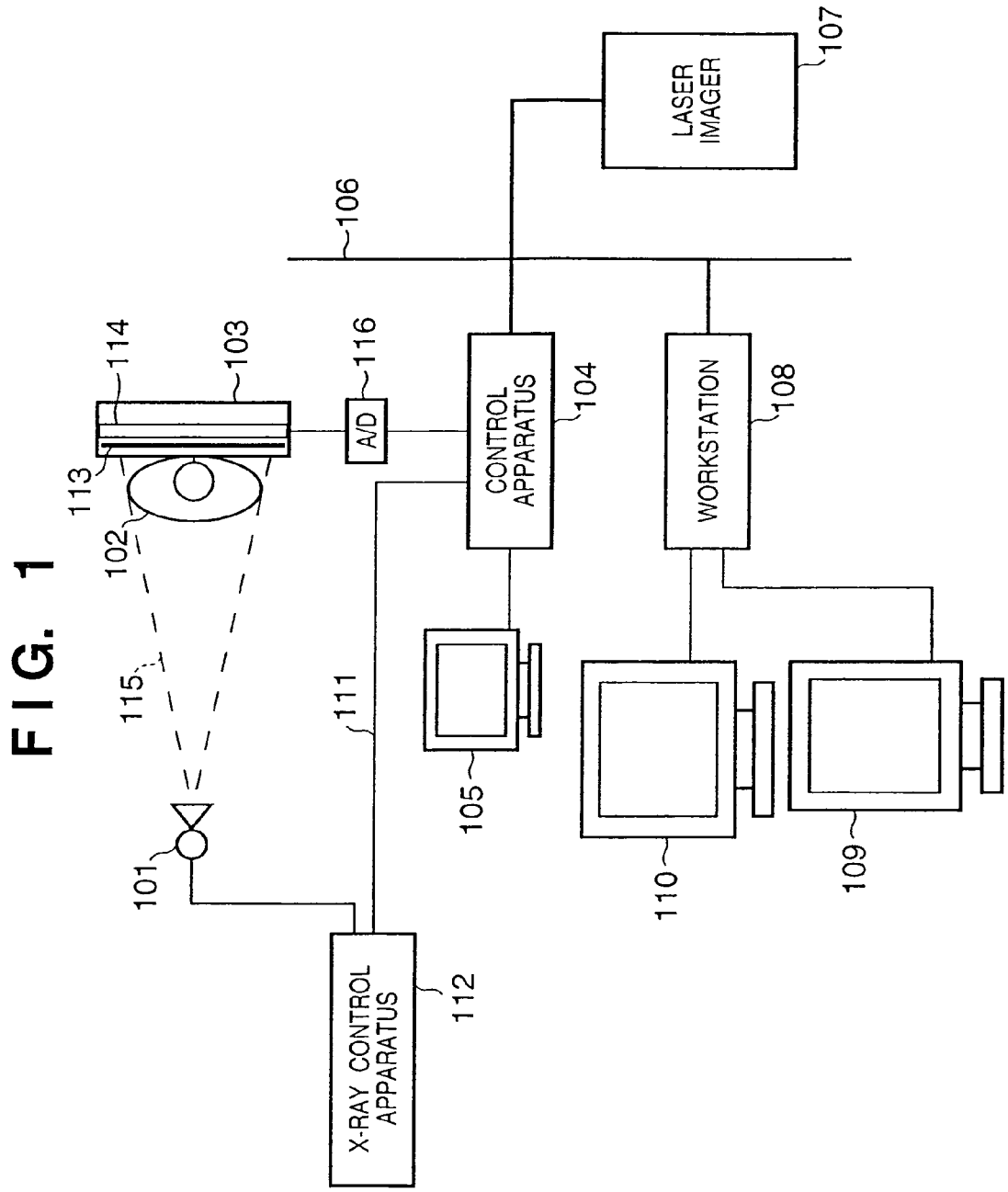
FIG. 1 is a view showing the schematic arrangement of a digital X-ray photographing system according to the first embodiment of the present invention.

FIG. 1 is a view showing the schematic arrangement of a digital X-ray photographing system according to the first embodiment of the present invention.

Referring to FIG. 1, an X-ray source 101 generates X-rays. An X-ray control apparatus 112 controls the tube voltage or tube current of a radiation tube for generating ray. X-rays 115 generated by the X-ray source 101 pass through a person 102 to be examined as a diagnosis object and enter an X-ray detection apparatus 103. At this time, the X-rays 115 pass through the person 102 to be examined and become incident on a phosphor 113 for converting the X-rays 115 into visible light. The X-rays 115 that have passed through the person 102 to be examined contain image information with different transmission amounts according to the sizes or shapes of bones and viscera or the presence/absence of a morbid portion in the person 102 to be examined. The X-rays 115 are converted into visible light by the phosphor 113 and enter an X-ray image sensing section 114. The X-ray image sensing section 114 as an example comprises a plurality of photoelectric conversion elements arrayed in the row and column directions. The X-ray image sensing section 114 converts image information light into an electrical signal, stores the signal, and outputs it as a digital image signal via an A/D converter 116. The image sensing time and driving method for the X-ray image sensing section 114 are controlled by a control apparatus 104 through a control line 111.

The digital image signal output from the A/D converter 116 is transferred to the control apparatus 104, subjected to predetermined image processing, and displayed on a simple image display apparatus 105. When examination is ended, the image which has undergone predetermined image processing is transferred to a laser imager 107 or a CRT diagnostic image processing work station 108 via a network 106. The image transferred to the laser imager 107 is formed on a film using a laser beam and developed. The image transferred to the CRT diagnostic image processing work station 108 is displayed on a portrait high-definition monitor 109 or a landscape high-definition monitor 110 together with an examination number, the name and date of birth of the person examined, and the like.

The relationship between a film and the X-ray detection apparatus 103 used in the first embodiment will be described next with reference to FIGS. 2 to 4.

Figure 2:
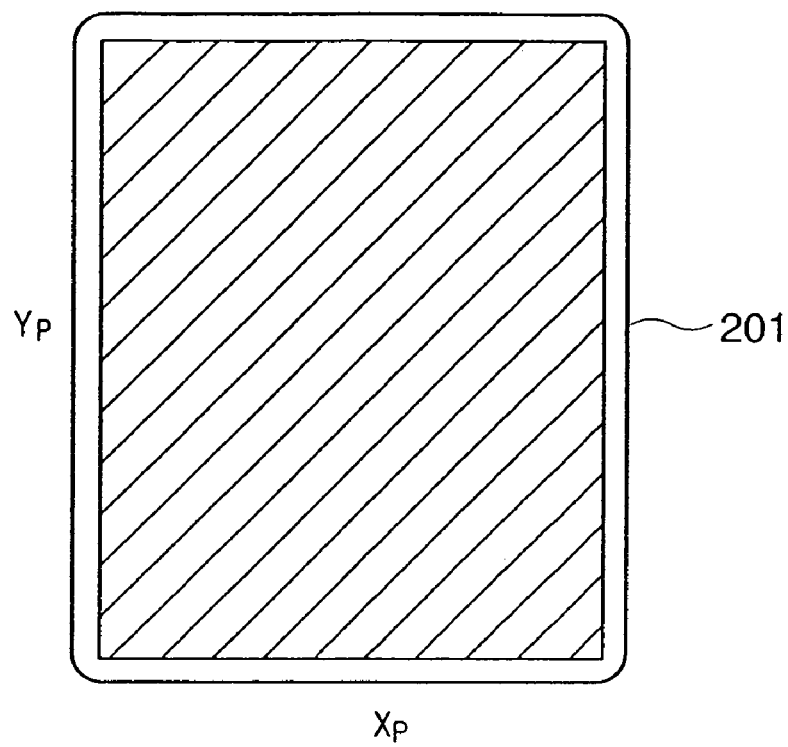
FIG. 2 is a view showing a portrait film with a regular size in the first embodiment of the present invention.

FIG. 2 is a view showing a portrait film with a regular size in the first embodiment of the present invention. FIG. 3 is a view showing a landscape film with a regular size in the first embodiment of the present invention. FIG. 4 is a view showing the X-ray detection apparatus according to the first embodiment of the present invention.

Figure 3:
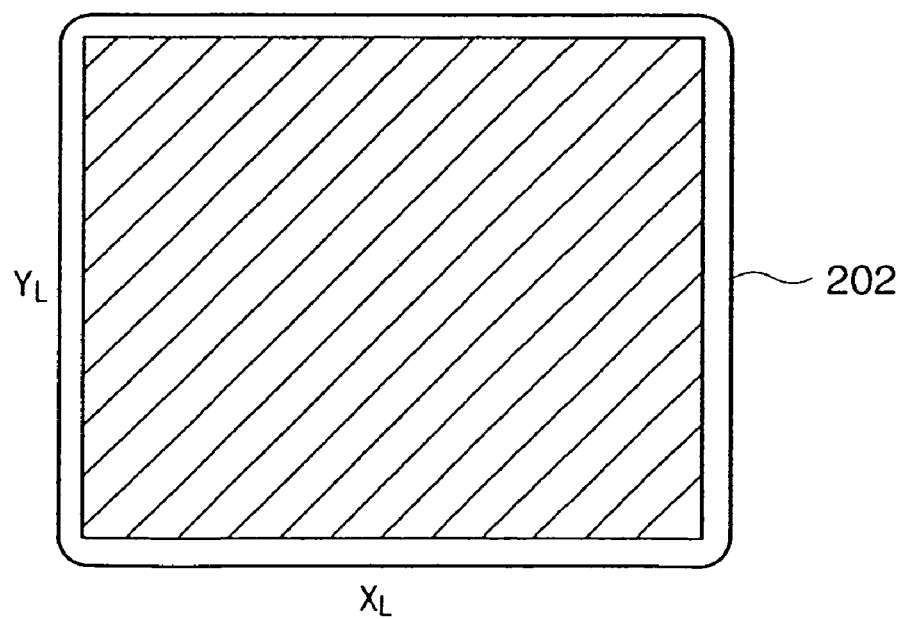
FIG. 3 is a view showing a landscape film with a regular size in the first embodiment of the present invention.
Figure 4:
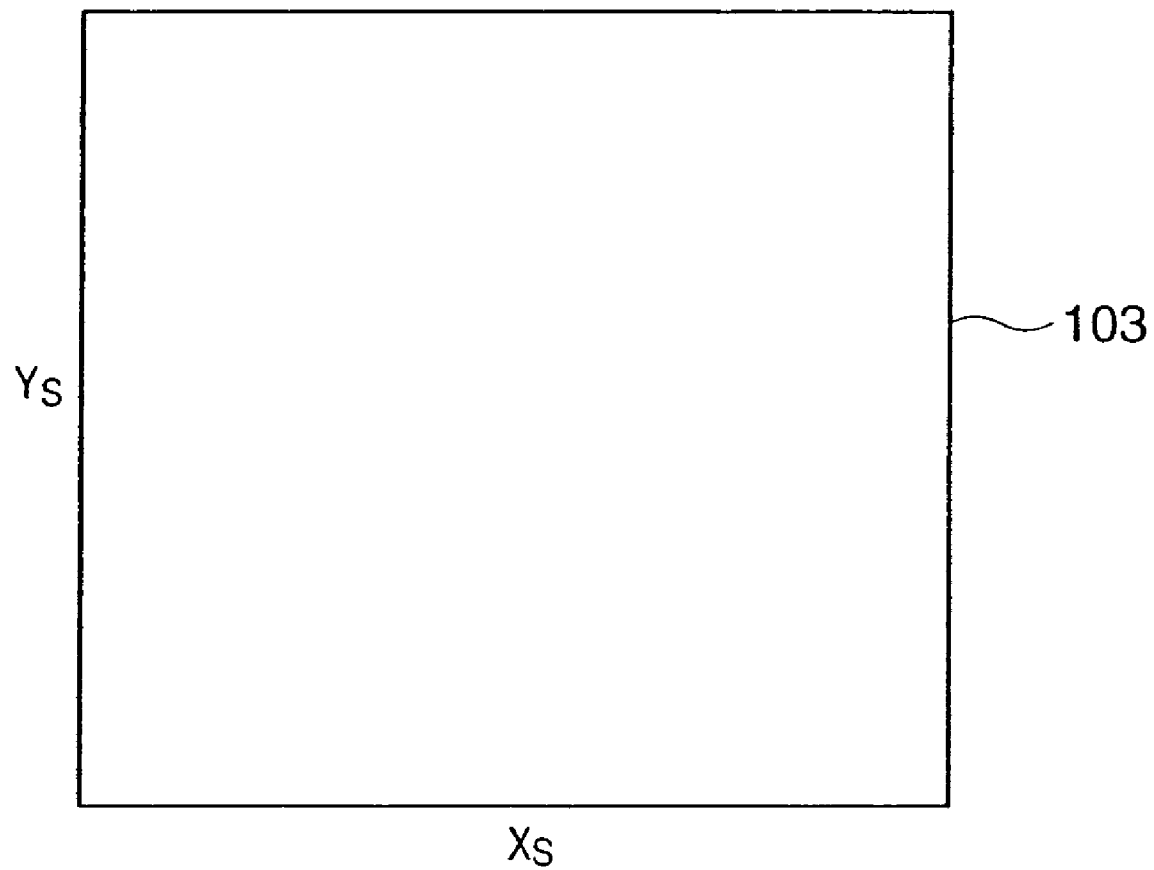
FIG. 4 is a view showing an X-ray detection apparatus according to the first embodiment of the present invention.

The X-ray detection apparatus 103 shown in FIG. 4 has a sufficiently larger size than the regular size of a portrait film 201 shown in FIG. 2 and that of a landscape film 202 shown in FIG. 3. The laser imager 107 cannot form an image in the entire area of a film. Generally, the laser imager 107 can form an image only in an area (effective image area) smaller than the film size. When the portrait film 201 has a width XP and a height YP, the landscape film 202 has a width XL and a height YL, and the X-ray detection apparatus 103 has a width XS and a height YS, XP≦XS, XL≦XS, YP≦YS, and YL≦YS.

The functional arrangement of the digital X-ray photographing system according to the first embodiment will be described next with reference to FIG. 5.

Figure 5:
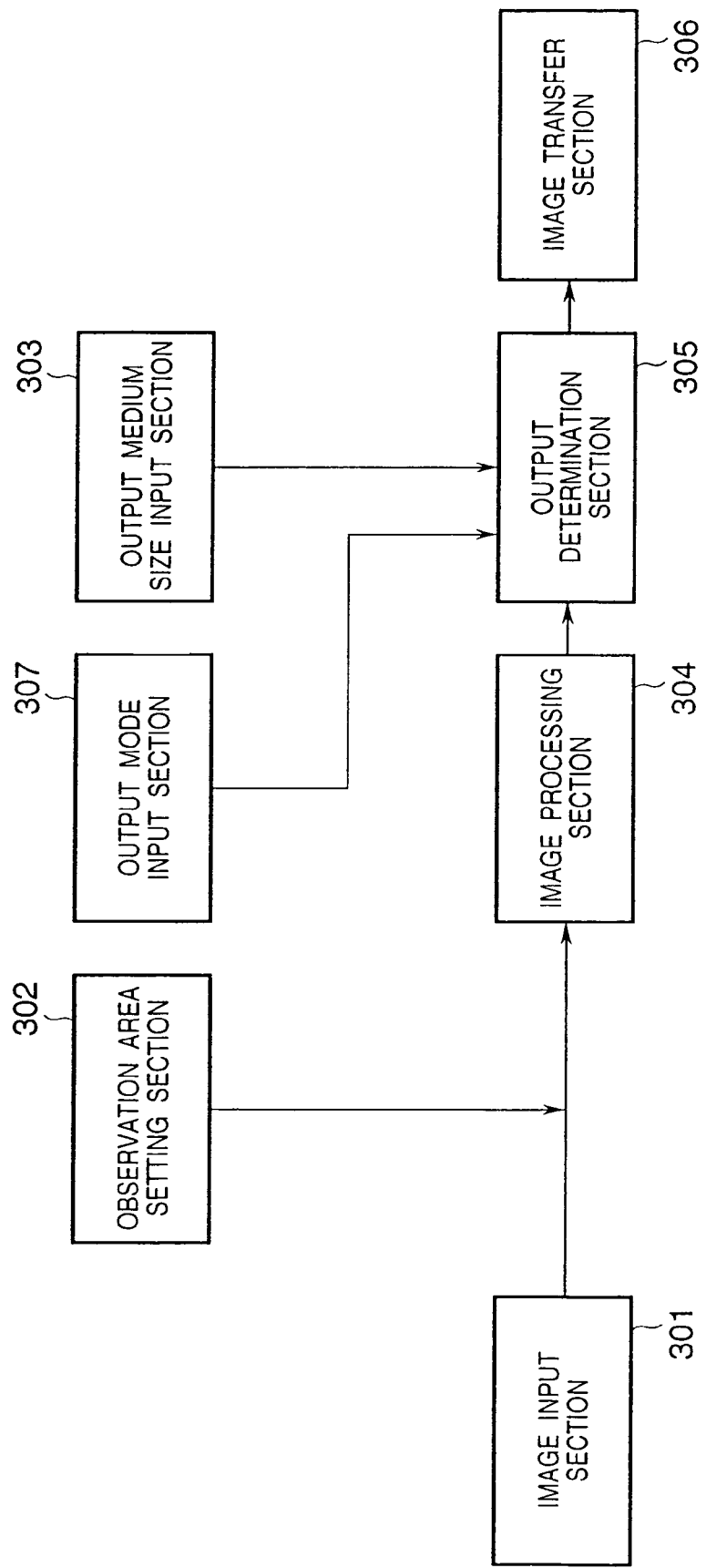
FIG. 5 is a block diagram showing the functional arrangement of the digital X-ray photographing system according to the first embodiment of the present invention.

Referring to FIG. 5, after radiation of X-rays, an image input section 301 acquires digital image data in the entire effective image area of the X-ray detection apparatus 103. The X-ray detection apparatus 103 may acquire, from a storage medium such as a hard disk, the digital image data in the effective image area, which has already been acquired from the X-ray detection apparatus 103. An observation area setting section 302 sets observation area setting information as information associated with an observation area to be displayed on an output medium such as a film. This observation area setting information is set using X-ray irradiation stop information obtained from the X-ray control apparatus 112, and then transferred from the X-ray control apparatus 112 to the control apparatus 104.

An image processing section 304 executes predetermined image processing. Various image processing operations such as gray-level processing or frequency processing suitable for observation by a doctor are performed. An output mode input section 307 inputs an output mode such that a life-size (actual size) image is output, an image is reduced and output, a life-size image is segmented into a plurality of films and output, or only one image is output by image extraction. An output medium size input section 303 inputs the size of the effective image area of the currently selected film. Since a portrait film and a landscape film may have different effective image area sizes, the size of the effective image area of each film is input. Although the output medium size input section 303 inputs the size of the effective image area of the film, the effective image area of the film may be acquired from the laser imager 107 via the network 106 online.

An output determination section 305 determines how to output the digital image data input by the image input section 301, on the basis of the contents input by the output mode input section 307 and output medium size input section 303. On the basis of the determination result of the output determination section 305, an image transfer section 306 transfers the digital image data to the laser imager 107 or CRT diagnostic image processing workstation 108.

Processing executed by the output determination section 305 of the first embodiment will be described next with reference to FIG. 6.

Figure 6:
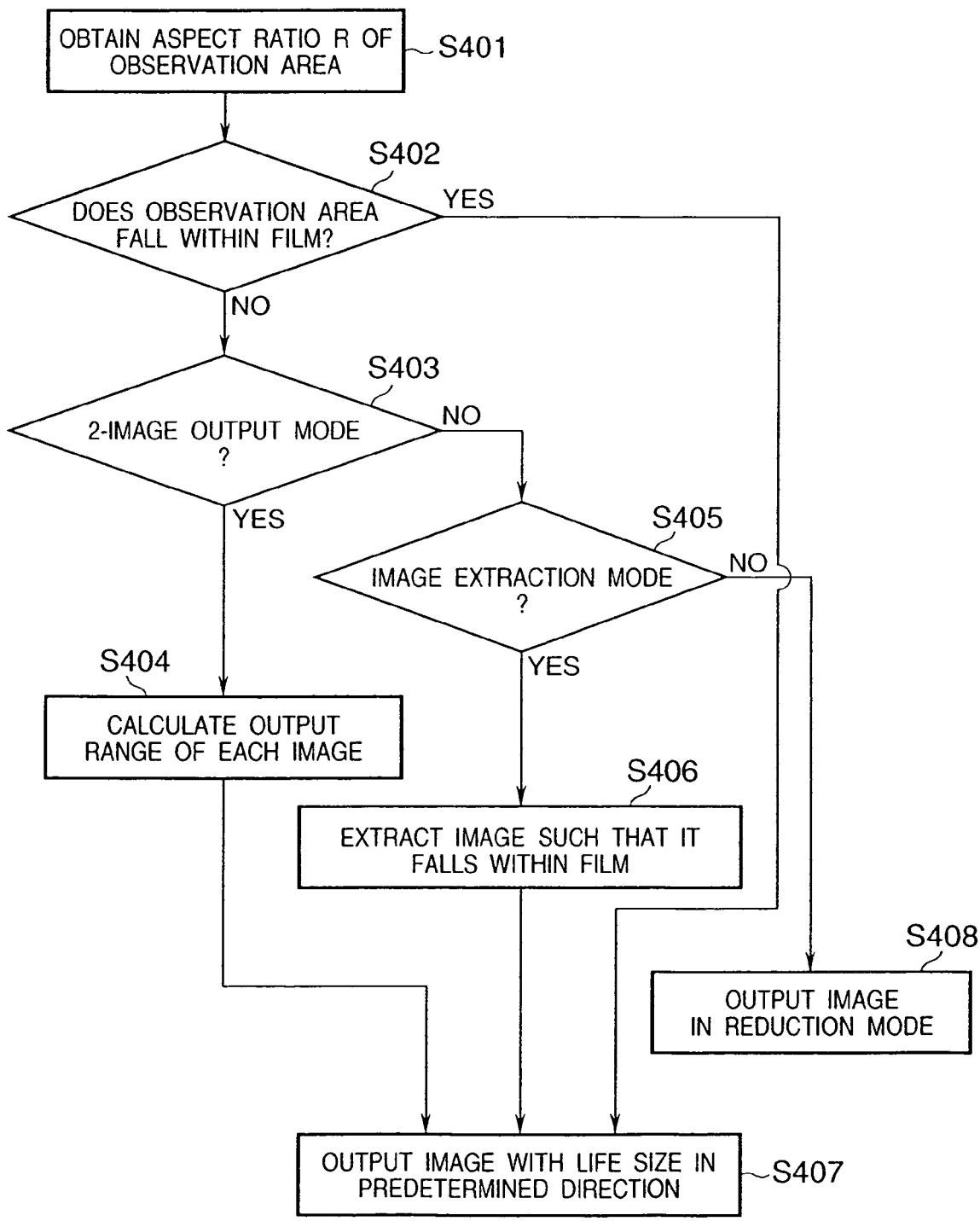
FIG. 6 is a flow chart showing processing executed by the output determination section of the first embodiment of the present invention.

FIG. 6 is a flow chart showing processing executed by the output determination section of the first embodiment of the present invention.

In step S401, an aspect ratio R of an observation area represented by observation area setting information set by the observation area setting section 302 is obtained. When the observation area has a width XR, a height YR, and the aspect ratio R, the aspect ratio R=YR/XR. When the aspect ratio R of the observation area is larger than 1.0, it is determined that the observation area is vertically elongated. When R<1.0, it is determined that the observation area is horizontally elongated. When R=1.0, it is determined that the observation area is square.

In step S402, using the size of the effective image area of the film, which is input by the output medium size input section 303, it is determined whether the observation area falls within the effective image area of the film. For either a portrait film or a landscape film, it is determined whether the observation area falls within the effective image area of the film. If the observation area falls within the effective image area (YES in step S402), the flow advances to step S407 to output a life-size image on the film in the direction based on the aspect ratio R of the observation area.

Figure 7:
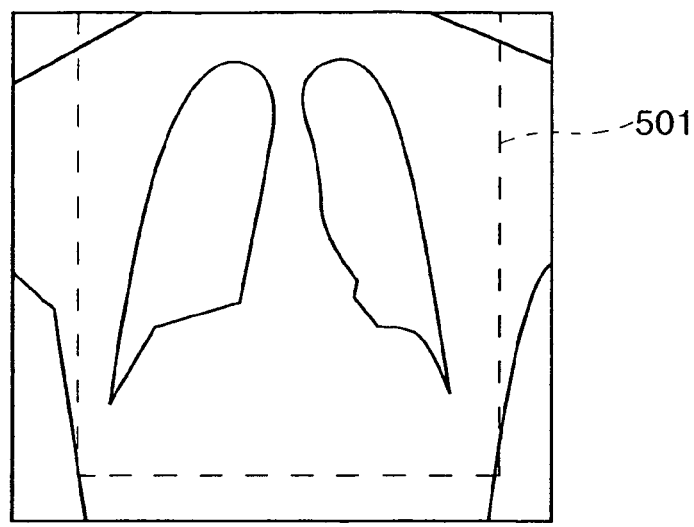
FIG. 7 is a view showing an observation area in the first embodiment of the present invention.
Figure 8:
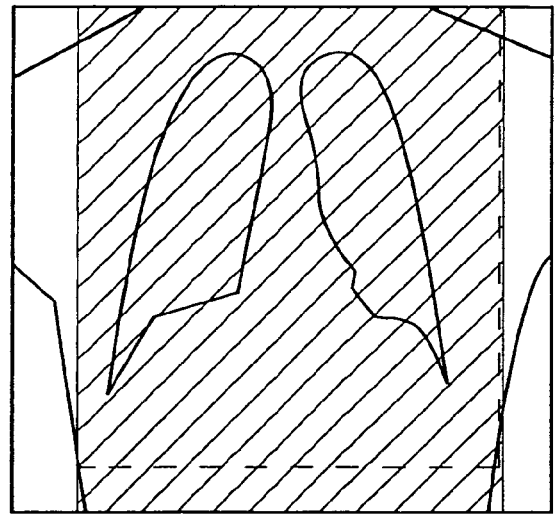
FIG. 8 is a view showing the effective image area of the portrait-film in the first embodiment of the present invention.
Figure 9:
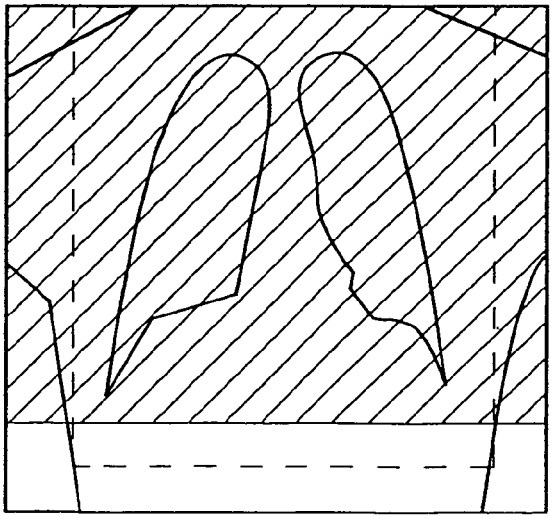
FIG. 9 is a view showing the effective image area of the landscape film in the first embodiment of the present invention.

More specifically, when an area 501 indicated by the dotted line in FIG. 7 is set by the observation area setting section 302 as the observation area, the hatched portion shown in FIG. 8 corresponds to the effective image area of a portrait film. The hatched portion shown in FIG. 9 corresponds to the effective image area of a landscape film. For the observation area 501 shown in FIG. 7, the aspect ratio R of the observation area is larger than 1.0, and an image is output using the portrait film shown in FIG. 8.

Figure 10:
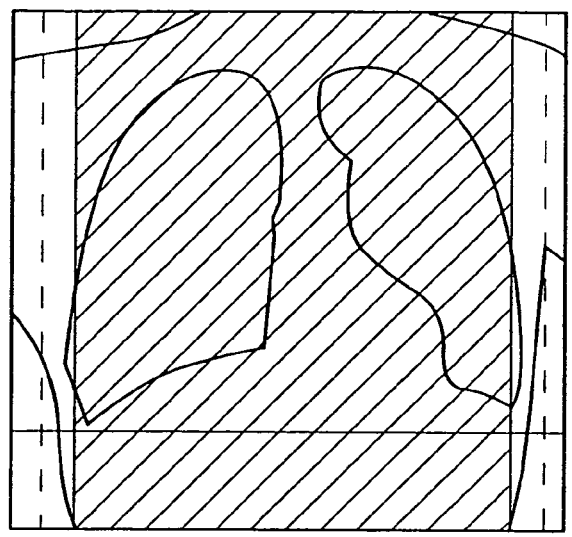
FIG. 10 is a view for explaining an example of determination of a film to be used for output in the first embodiment of the present invention.
Figure 11:
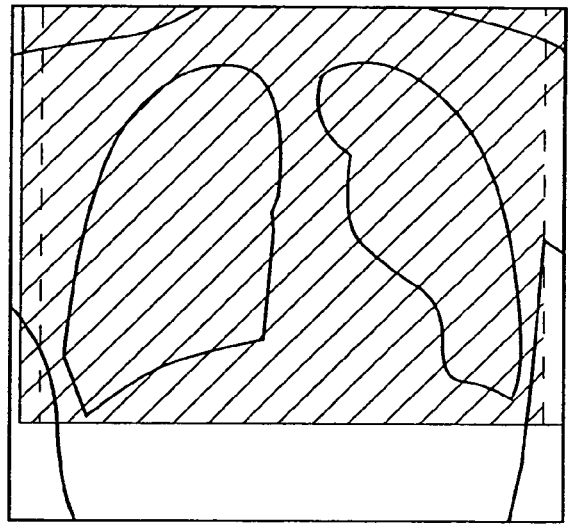
FIG. 11 is a view showing an example of image formation on the landscape film in the first embodiment of the present invention.

When an area indicated by the dotted line in FIG. 10 is set by the observation area setting section 302 as the observation area, the aspect ratio R of the observation area is smaller than 1.0, and an image is output using the landscape film shown in FIG. 11.

When it is determined in step S402 that the observation area does not fall within the effective image area of the film (NO in step S402), the flow advances to step S403 to confirm the output mode set by the output mode input section 307. In the first embodiment, it is determined in step S403 whether a 2-image output mode is set. In addition, it is determined in step S405 whether an image extraction output mode is set.

When the 2-image output mode is not set (NO in step S403) and the image extraction output mode is not set (NO in step S405), i.e., when the 1-image output mode and the reduction output mode are set, the image is reduced and output such that the observation area falls within the effective image area of the film in step S408.

Figure 12:
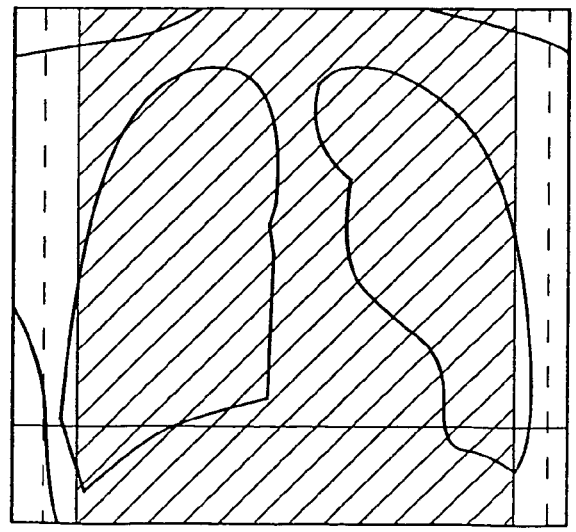
FIG. 12 is a view for explaining an image switching output mode in the first embodiment of the present invention.

Assume that the 2-image output mode is not set (NO in step S403) and the image extraction output mode is set (YES in step S405), i.e., the 1-image output mode and the life-size output mode are set. In this case, in step S406, the film to be used is determined on the basis of the aspect ratio R of the observation area, and an image portion that falls outside the effective image area of the film is extracted using, as a reference, the center of the effective image area of the film and the center of the observation area. In step S407, the extracted life-size image is output. In the example shown in FIG. 12, the image portion between the right boundary line of the effective image area and the right boundary line of the observation area and that between the left boundary line of the effective image area and the left boundary line of the observation area are extracted in step S406. In the example shown in FIG. 13, the image portion between the lower boundary line of the effective image area and the lower boundary line of the observation area is extracted in step S406.

In the first embodiment, an image portion that falls outside the effective image area is extracted using, as the reference, the center of the effective image area of the film. However, the reference is not limited to the center of the effective image area. Various positions can be set as the reference to shift the effective image area to the upper or lower side or the left or right side. This reference can be set by the output mode input section 307.

When the 2-image output mode is set (YES in step S403), in step S404, using films determined on the basis of the aspect ratio R of the observation area, the overlap portion of the effective image areas of the films is calculated. The output ranges of images to be output to the two films are determined on the basis of the overlap portion. In step S407, images within the determined output ranges are output to the two films, respectively. FIG. 14 shows the 2-image output mode using portrait films. In this example, the overlap portion of the effective image areas is calculated from the image output range obtained by aligning the effective image area of one film to the right boundary line of the observation area and that obtained by aligning the effective image area of the other film to the left side of the observation area.

In the processing described with reference to FIG. 6, it is determined whether the output mode is the 2-image output mode. When the X-ray detection apparatus 103 is much larger than the effective image area of a film, not the 2-image output mode but a multi-image output mode for outputting three or more images may set to output images.

As described above, according to the first embodiment, in the digital X-ray photographing system having the X-ray detection apparatus 103 larger than the regular size of a film as the output medium, even when the image of the person to be does not fall within the regular-size film, an image corresponding to the entire observation area can be output by one cycle of exposure in accordance with the set output mode, so the X-ray dose for the person to be examined can be reduced. In addition, since the technician as the operator of the X-ray photographing system need not exchange the X-ray detection apparatus to an apparatus with the same size as the regular size of a film or change the direction of the film, the entire examination time can be shortened.

Second Embodiment

Figure 15:
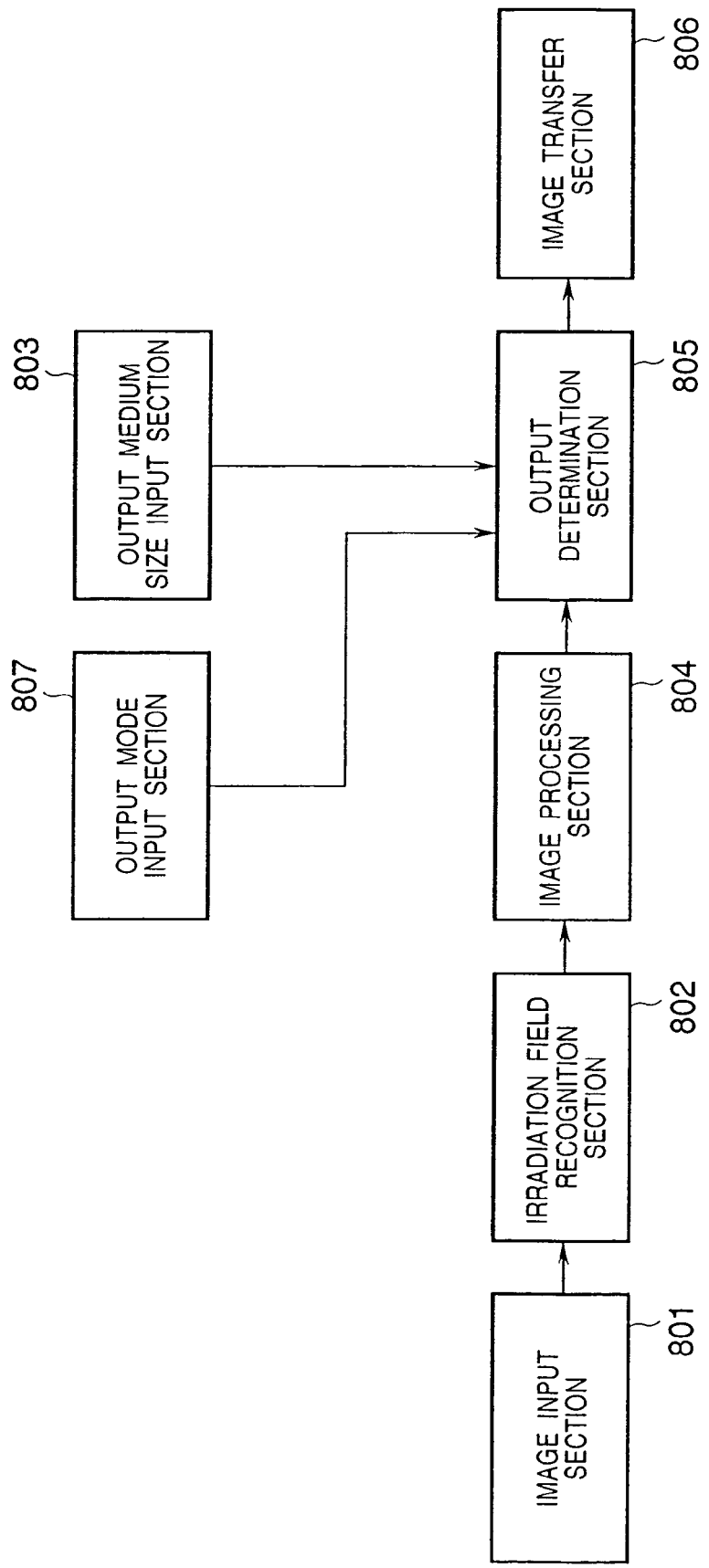
FIG. 15 is a block diagram showing the functional arrangement of a digital X-ray photographing system according to the second embodiment of the present invention.

In the first embodiment, the observation area setting information is set by the observation area setting section 302 using the X-ray irradiation stop information obtained from the X-ray control apparatus 112. However, this is not always necessary. For example, as shown in FIG. 15, on the basis of digital image data acquired by an image input section 801, an irradiation field recognition section 802 automatically acquires an area where an X-ray detection apparatus 103 is irradiated with X-rays, and determines the area as an observation area. The processing described in the first embodiment is executed for this observation area. As the irradiation field recognition section 802, for example, a method disclosed in Japanese Patent Application No. 10-243020 proposed by the present applicant can be applied.

The image input section 801, an image processing section 804, output mode input section 807, output medium size input section 803, output determination section 805, and image transfer section 806 correspond to the image input section 301, image processing section 304, output mode input section 307, output medium size input section 303, output determination section 305, and image transfer section 306 of the first embodiment shown in FIG. 5, respectively, and the functions thereof are the same as described in the first embodiment.

As described above, according to the second embodiment, even when X-ray irradiation stop information cannot be acquired from the X-ray control apparatus 112, the same effect as described in the first embodiment can be obtained by using the irradiation field recognition section 802.

Third Embodiment

Figure 18:
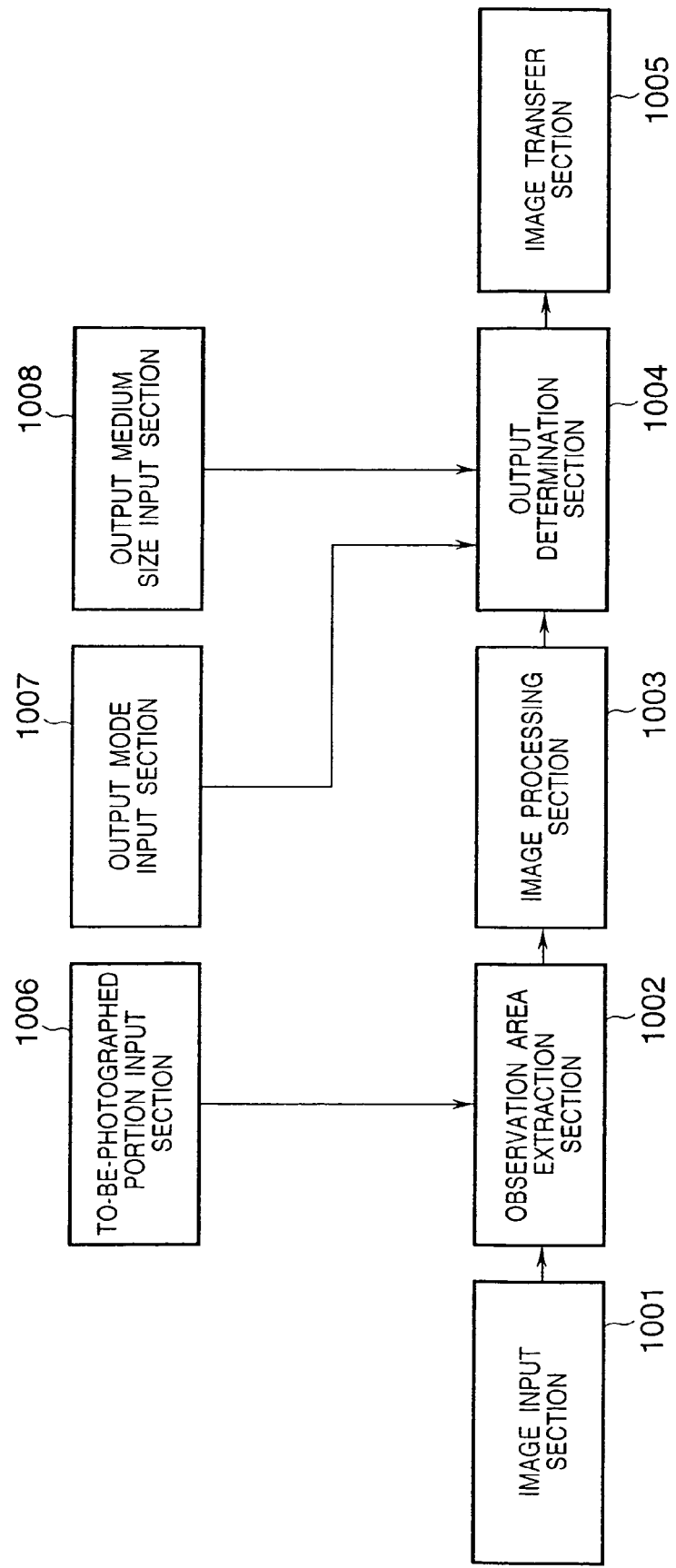
FIG. 18 is a block diagram showing the functional arrangement of a digital X-ray photographing system according to the third embodiment of the present invention.

In the first embodiment, the observation area setting information is set by the observation area setting section 302 using the X-ray irradiation stop information obtained from the X-ray control apparatus 112. However, this is not always necessary. For example, as shown in FIG. 18, observation area setting information may be obtained by setting portion information input from a to-be-photographed portion input section 1006. An observation area extraction section 1002 automatically extracts the basic observation area for the doctor from that portion. An observation area is set on the basis of the basic observation area, thereby obtaining the observation area setting information. FIGS. 16 and 17 show this example. FIG. 16 shows the front image of a chest. FIG. 17 shows the side image of the chest. In both cases, an area (an area indicated by a thin dotted line) including the area of lungs is the basic observation area for the doctor. This basic observation area is extracted by the method described in, e.g., Hasegawa, Toriwaki, and Fukumura, "Software System AISCR-V3 for Automatically Screening Indirectly Photographed Thoracic Radiograph", IEICE Transactions J66-D10, (1983). In this method, after the area of lungs is roughly extracted, the circumscribed rectangular area of the lung area is extracted as the basic observation area. After that, the area is enlarged by N (N is a non-integer) using the center of the basic observation area as a reference, thereby acquiring an observation area (indicated by a bold dotted line). The processing described in the first embodiment is performed for this observation area.

An image input section 1001, image processing section 1003, output mode input section 1007, output medium size input section 1008, output determination section 1004, and image transfer section 1005 correspond to the image input section 301, image processing section 304, output mode input section 307, output medium size input section 303, output determination section 305, and image transfer section 306 of the first embodiment shown in FIG. 5, respectively, and the functions thereof are the same as described in the first embodiment.

As described above, according to the third embodiment, the basic observation area is automatically extracted in accordance with the portion to be photographed, and the observation area is set no the basis of the basic observation area. Unlike the first and second embodiments in which the observation area is obtained on the basis of the X-ray irradiation stop information, a necessary minimum area can be acquired without missing the area necessary for the doctor's diagnosis. Hence, a smaller output medium such as a film can be selected to reduce running cost.

As has been described above, according to the above embodiments of the present invention, an image processing system and a control method for the system, a photographing system and a control method for the system, and a computer-readable memory, which can efficiently photograph without any increase in the X-ray dose for the person to be examined, can be provided.

Fourth Embodiment

In the fourth embodiment, the image processing apparatus of the present invention is applied to an X-ray imaging apparatus.

Figure 19:
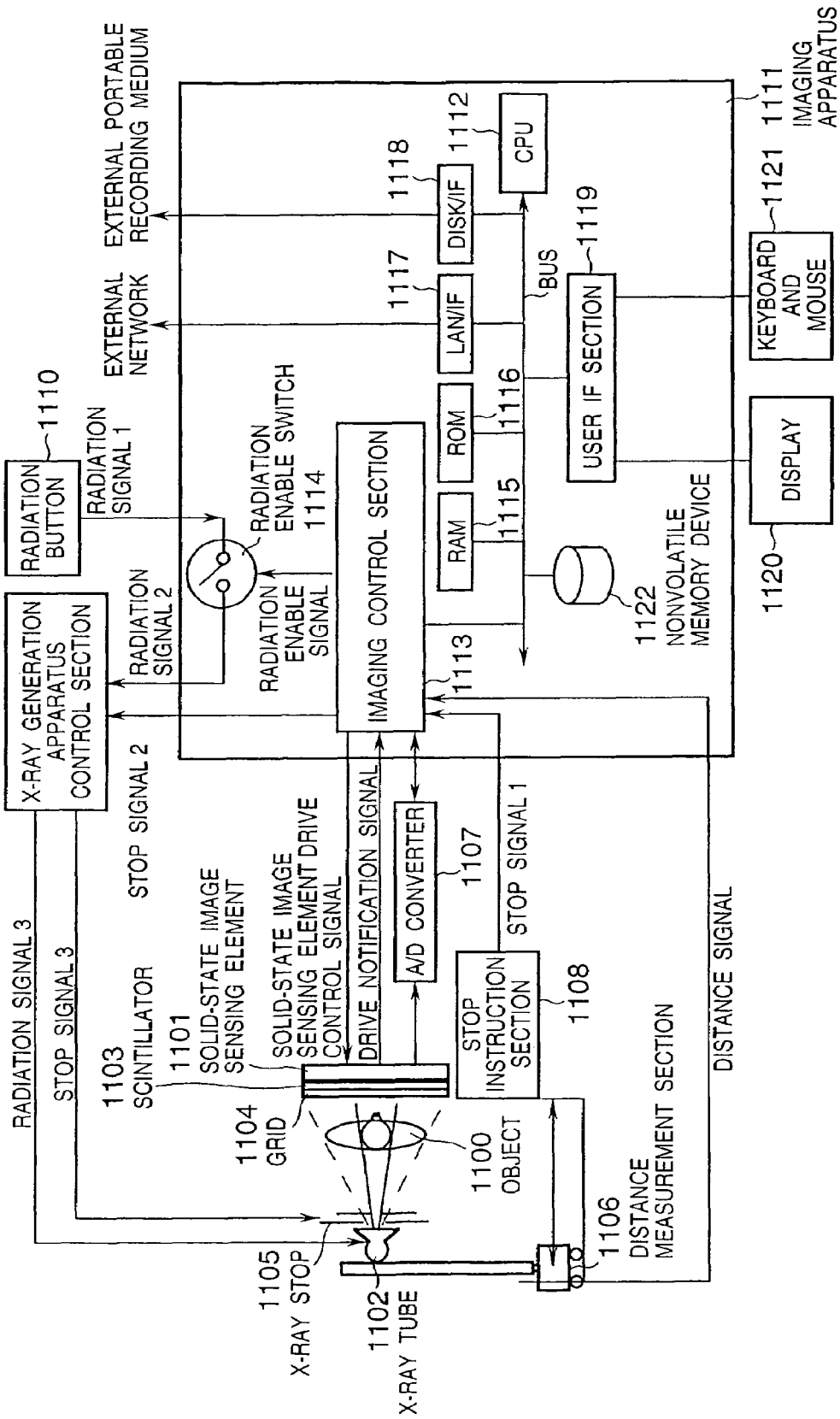
FIG. 19 is a block diagram showing the arrangement of an X-ray imaging apparatus.

FIG. 19 is a block diagram showing the arrangement of the X-ray imaging apparatus. The operator sets an object 1100 to be photographed between a solid-state image sensing element 1101 and an X-ray tube 1102. Next, the operator selects the portion to be photographed using a user interface (the user interface is constructed by a display IF section 1119, display 1120, and keyboard and mouse 1121). With this operation, the object setting style, i.e., PS photographing (X-rays are radiated from the backside to the front) and AP photographing (X-ray are radiated from the front to the backside) is instructed. Simultaneously, an imaging control section 1113 applies a voltage to the solid-state image sensing element 1101 using a solid-state image sensing element drive control signal, thereby preparing for image input to the solid-state image sensing element 1101.

The operator moves the X-ray tube 1102 to a position separated from the solid-state image sensing element 1101 by an appropriate distance. At this time, the distance (distance signal) between the solid-state image sensing element 1101 and the X-ray tube 1102 is input from a distance measurement section 1106 to the imaging control section 1113.

The operator adjusts the X-ray stop-down amount using a stop instruction section 1108 such that the to-be-photographed portion of the object is captured. Stop signal 1 from the stop instruction section 1108 is transmitted to the imaging control section 1113, stop signal 2 to an X-ray generation apparatus control section 1109, and stop signal 3 to an X-ray stop 1105 to control its opening/closing degree. The X-ray stop 1105 has a rectangular shape. The open/close amount of the X-ray stop 1105 can be adjusted in both the vertical and horizontal directions. Whether the portion of the object 1100 is appropriately illuminated through the X-ray stop 1105 can be determined using lamp light.

A radiation button 1110 serves as a trigger for causing the X-ray tube 1102 to generate X-rays. Radiation signal 1 generated by the radiation button 1110 is temporarily input to the imaging control section 1113 in an imaging apparatus 1111. The imaging control section 1113 confirms whether the solid-state image sensing element 1101 is ready for forming an image of input X-rays, on the basis of a drive notification signal from the unit including the solid-state image sensing element 1101, and then generates a radiation enable signal. The radiation enable signal turns on a radiation enable switch 1114 to connect radiation signal 1 to radiation signal 2. The radiation signal is generated using the second switch of the radiation button (the radiation button of the X-ray generation apparatus constitutes a two-stroke switch: a voltage is applied to the X-ray generator at the first stroke position (first switch), and X-rays are radiated at the second stroke position (second switch)).

Radiation signal 2 is input to the X-ray generation apparatus control section 1109. As soon as the apparatus becomes ready for radiating X-rays, the X-ray generation apparatus control section 1109 outputs radiation signal 3 to cause the X-ray tube 1102 to generate X-rays. The transmitted rays of the radiated X-rays are input to the solid-state image sensing element 1101 through a grid 1104 and scintillator 1103 as an image.

The solid-state image sensing element 1101 generates an electrical signal corresponding to this image. This signals is read out, converted into a digital signal by an A/D converter 1107, and transferred to the imaging control section 1113. The imaging control section 1113 is managed by a CPU 1112. The CPU 1112 is connected, via a bus, to not only the imaging control section 1113 but also a RAM 1115, ROM 1116, LAN/IF 1117, DISK/IF 1118, nonvolatile memory device 1122, and user IF section 1119.

In this embodiment, a hard disk is used as the nonvolatile memory device 1122. The user IF section 1119 has the display 1120 and keyboard and mouse 1121 to interface with the user. The image (digital image) input from the A/D converter 1107 to the imaging control section 1113 is temporarily stored in the RAM 1115 and subjected to various processing operations (to be described later) by the CPU 1112.

Figure 20:
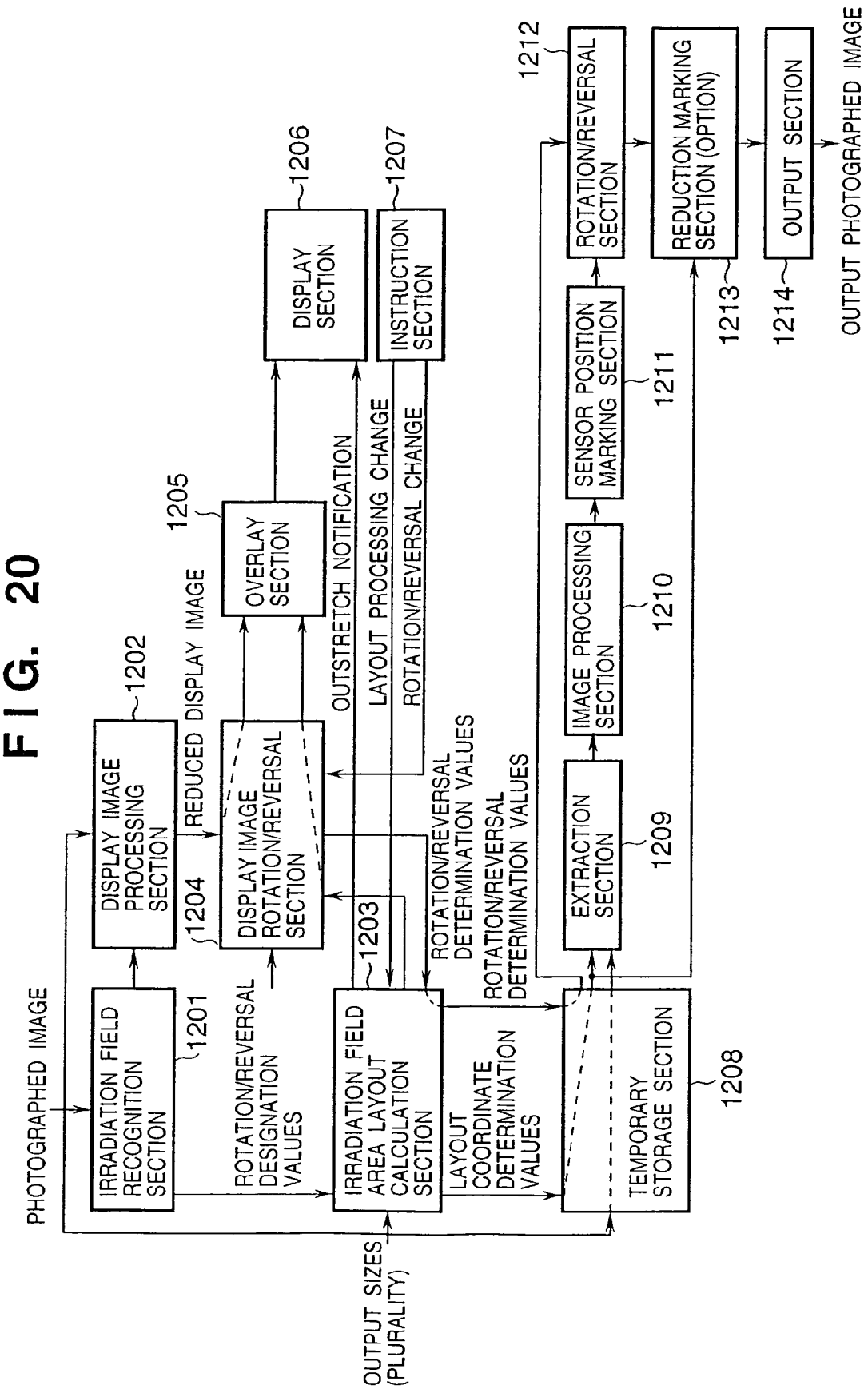
FIG. 20 is a block diagram for explaining irradiation field area layout and sensor position marking processing.

FIG. 20 is a block diagram for explaining irradiation field area layout and sensor position marking processing. Processing shown in FIG. 20 is realized when the CPU 1112 executes a control program stored in the ROM 1116.

An irradiation field recognition section 1201 recognizes the irradiation field of the photographed image and calculates the irradiation field area. Various methods can be used to recognize the irradiation field. For example, the method proposed in Japanese Patent Application No. 10-243020 by the present applicant can be used. This will be briefly described. With an arrangement comprising a calculation means for calculating the first derivative of the gray-scale value representing each two adjacent areas of three parallel square areas and calculating the second derivative from the calculated first derivative, a calculation area determination means for determining the three square areas, a storage means for storing the second derivative calculated by the calculation means, and a determination means for determining one end point of an irradiation area from the second derivative stored in the storage means, an irradiation area is easily and accurately extracted from a radiographic image. When the irradiation field is recognized by the irradiation field recognition section 1201, the recognition result (irradiation field area information) is supplied to a display image processing section 1202.

On the basis of the irradiation field area information from the irradiation field recognition section 1201, the display image processing section 1202 processes the image such that appropriate contrast is set within the irradiation field area. For example, data is decimated to generate a reduced display image. This processing is not directly associated with this embodiment, and a detailed description thereof will be omitted.

The irradiation field area information representing the irradiation field recognition result from the irradiation field recognition section 1201 is also supplied to an irradiation field area layout calculation section 1203. The irradiation field area layout calculation section 1203 calculates the irradiation field area layout on the basis of some output sizes set in advance. The algorithm of calculation will be described later. In the output from the irradiation field area layout calculation section 1203, the irradiation field area of the original photographed image falls within the selected output size.

Figures 21, 22:
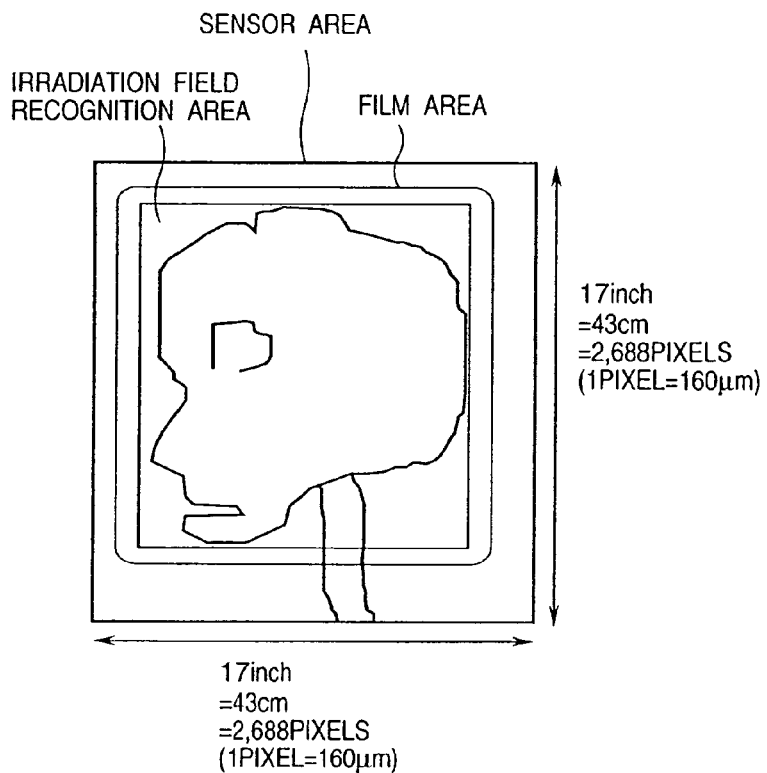
FIG. 21 is a view showing an example of layout of an irradiation field area.
FIG. 22 is a view for explaining output sizes set in advance.

FIG. 21 is a view showing an example of layout of the irradiation field area. Referring to FIG. 21, the large size (35-cm square) is selected as the output size (film area), and the irradiation field area is laid out within the output size.

FIG. 22 is a view for explaining output sizes set in advance. In this embodiment, five designated sizes are prepared, as shown in FIG. 22. The irradiation field area layout calculation section 1203 selects an appropriate one of the output sizes. For example, referring to FIG. 21, the large size is selected from these designated sizes. This size is optimum because an excess area becomes large in a larger film size, and the irradiation field area does not fall within a smaller film size.

Note that, in FIGS. 21 and 22, the number of pixels is accurate. However, the values with units of "inch" and "centimeter" are not accurate.

Figure 26:
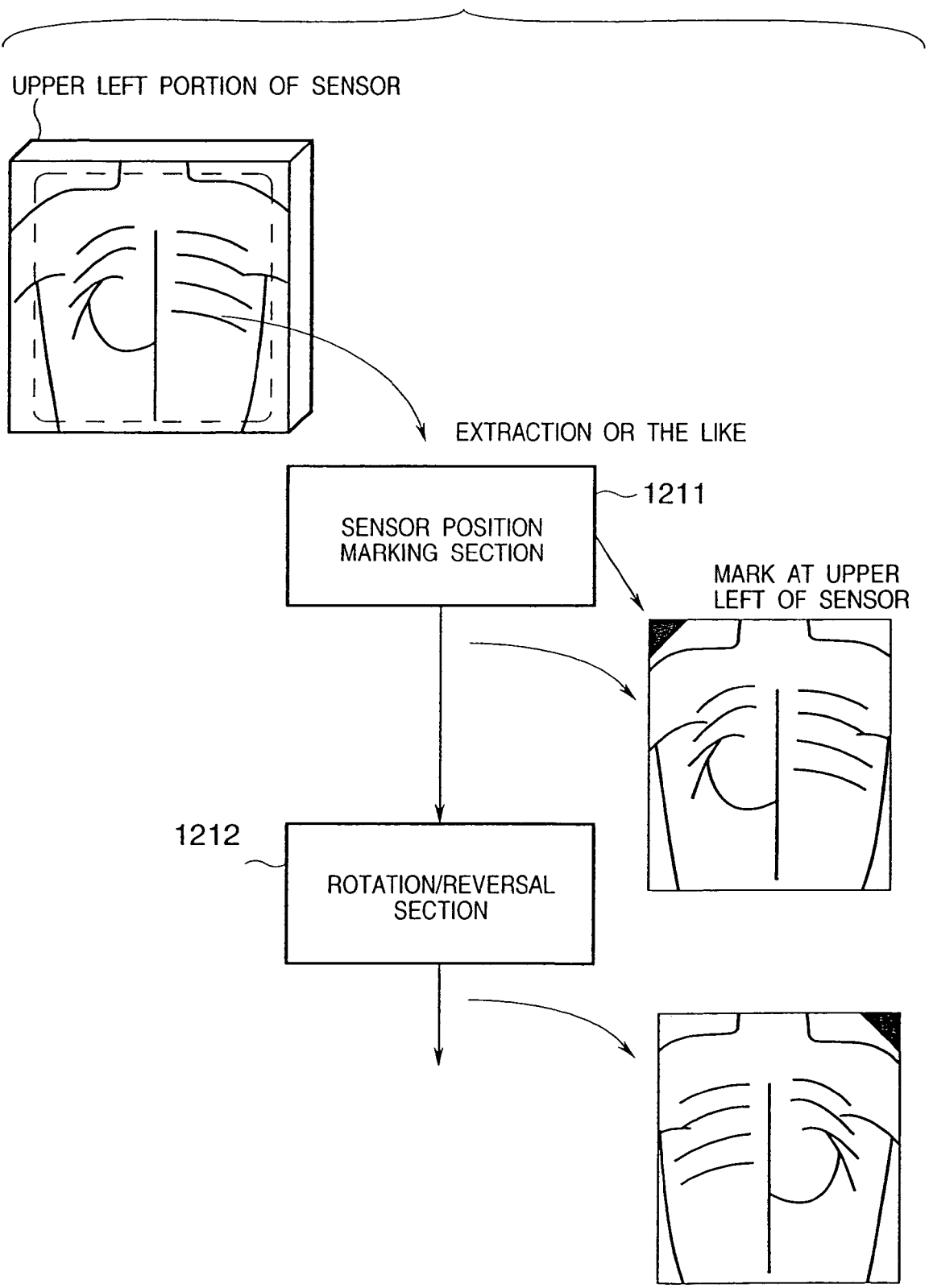
FIG. 26 is a view for explaining sensor position marking by a sensor position marking section.

Referring back to FIG. 20, the irradiation field area layout calculation section 1203 calculates the layout of the irradiation field area in the designated size. The calculation result is supplied to a display image rotation/reversal section 1204. The display image rotation/reversal section 1204 rotates/reverses the reduced display image on the basis of a rotation/reversal value instructed at the time of photographing. For example, as shown in FIG. 26, when the operator photographs the object in the PA photographing mode (from the backside to the front), and the photographed image is simply displayed, the image is reversed, unlike an image normally observed by a doctor. For example, the heart is displayed on the left side. Hence, in PA photographing, the image must be reversed and then displayed. Rotation processing is done to correct a vertically inverted image because an image may be inverted in the vertical direction depending on the direction of the head of the to-be-examined person on the bed. Since the PA and AP photographing modes are used even on a bed, reversal processing is necessary due to the same reason as described above.

The display image rotation/reversal section 1204 must convert the coordinate system in consideration of the reduction ratio for display and rotation/reversal even for irradiation field area layout coordinates. The conversion result is transmitted to an overlay section 1205.

The overlay section 1205 displays a rectangle based on the irradiation field area layout coordinates reduced, rotated, and reversed, which is overlaid on the reduced display image rotated and reversed. The image is displayed on a display section 1206. This display will be described later with reference to FIG. 30.

When the irradiation field area layout calculation section 1203 cannot set the entire irradiation field area within the maximum output size, the operator is notified that the irradiation field area does not fall within the output size. In this embodiment, the display section 1206 displays a warning message. In this case, the operator can take one of the following three solutions.

Figure 23:
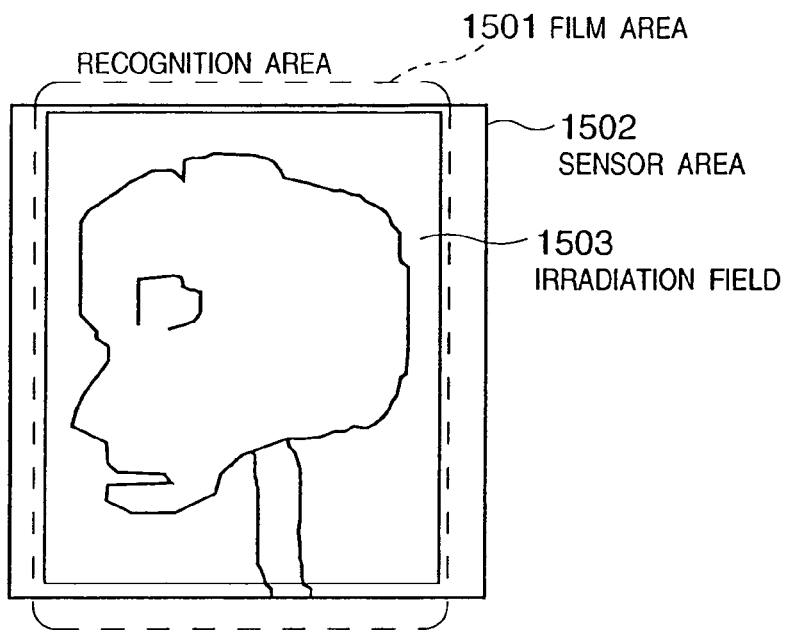
FIG. 23 is a view for explaining an irradiation field.

(1) The image in the irradiation field area is reduced such that the irradiation field area falls within the maximum output size. In this case, the image is output not in life size but in a smaller size. FIG. 23 is a view for explaining reduction of the irradiation field. A film area 1501 indicated by the broken line in FIG. 23 is expressed to be large relative to an irradiation field area 1503. In actual processing, the irradiation field area 1503 is reduced such that it falls within the film area 1501, so the film output has a size smaller than life size. A sensor area 1502 is the area of the solid-state image sensing element 1101 where an image can be input.

Figure 24:
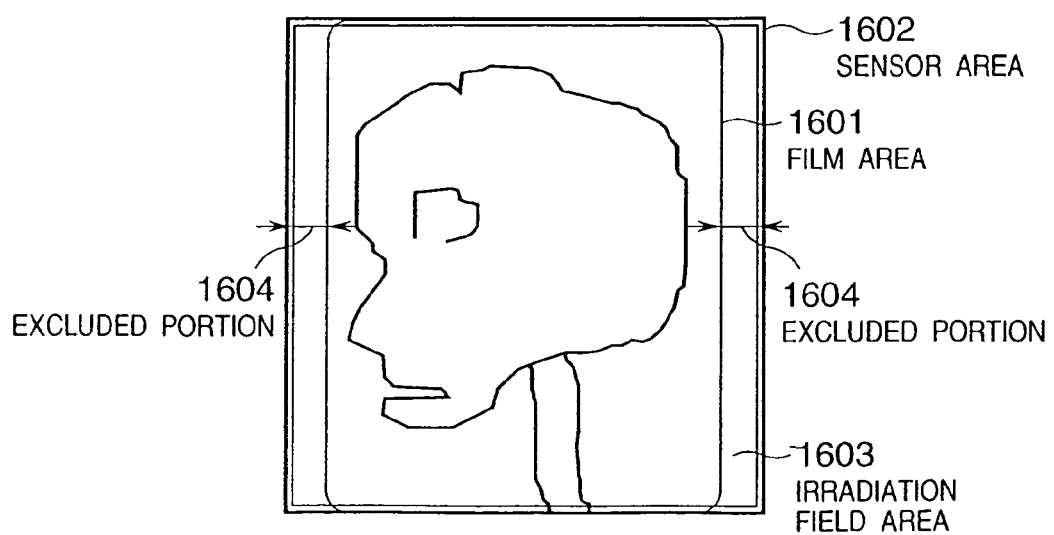
FIG. 24 is a view for explaining processing of reducing the range of the irradiation field area.

(2) The range of the irradiation field area is restricted such that the range falls within the film area. FIG. 24 is a view for explaining reduction of the range of the irradiation field area. With this processing, as shown in FIG. 24, those portions of an irradiation field area 1603 which protrude from a film area 1601 are excluded as excluded portions 1604.

Figure 25:
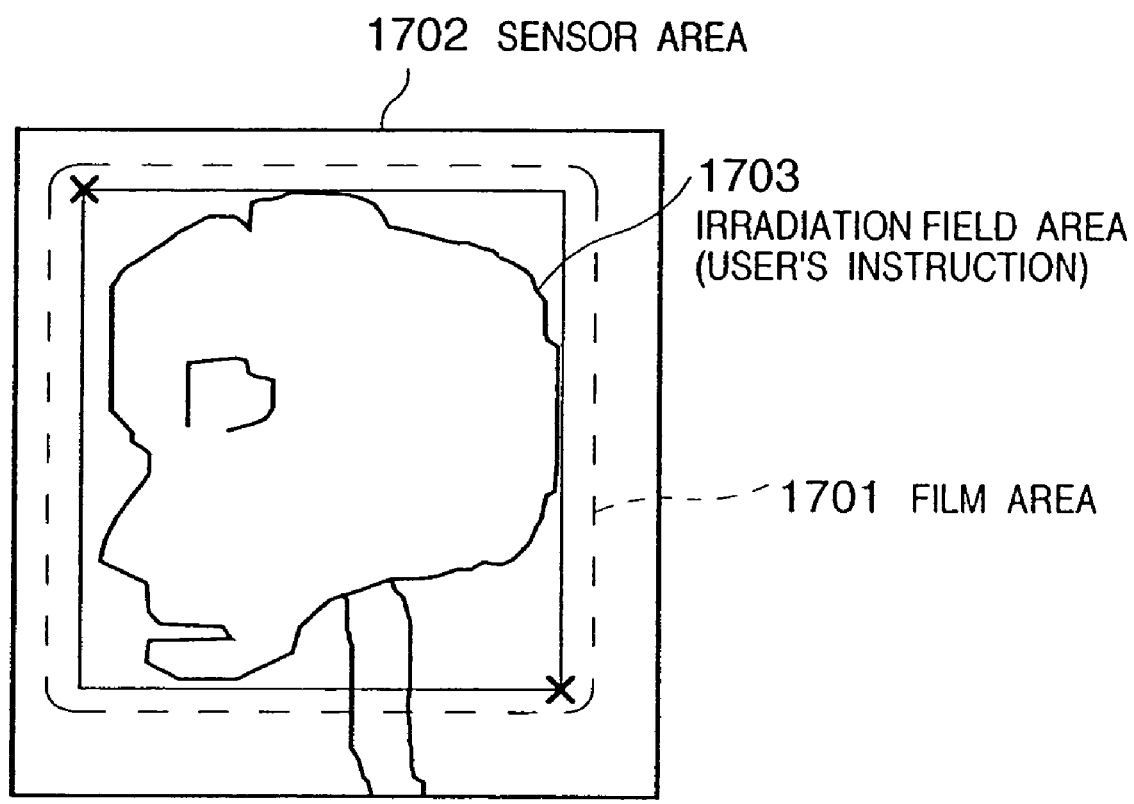
FIG. 25 is a view for explaining processing of limiting the irradiation field area by an operator.

(3) The operator designates a limited irradiation field area. FIG. 25 is a view for explaining limitation of the irradiation field area by the operator. In this case, the operator points, with the mouse, diagonal vertices of a rectangle to be set as an irradiation field area. Referring to FIG. 25, when the operator points two positions indicated by x, an irradiation field area 1703 is determined. This irradiation field area 1703 is used in place of the irradiation field area obtained by the irradiation field recognition section 1201. That is, when the operator designates the irradiation field area 1703 smaller than a film area 1701, normal processing is performed. In this example, a large size including the irradiation field area 1703 is designated. To designate the size, a size with a minimum residual is automatically selected.

The above change in layout processing is designated to the irradiation field area layout calculation section 1203 using an instruction section 1207 (the display IF section 1119 in this case) to achieve the exceptional operation.

Sometimes although the operator has photographed the object in the PA (from the backside to the front) photographing mode, the object must be photographed in the AP (from the front to the backside) photographing mode in actually determining the direction of the patient because of his/her condition of the disease. In this case, the image must be reversed after photographing. The instruction section 1207 can instruct the display image rotation/reversal section 1204 to reverse or rotate (rotation/reversal change) the image. Upon receiving the rotation/reversal change instruction, the display image rotation/reversal section 1204 rotates or reverses the image in accordance with the instruction and re-displays the image.

When the operator appreciates the image layout finally, the layout calculation is determined. Two methods can be used to do this. The operator explicitly inputs an instruction from the instruction section 1207, or the time is out before the operator inputs an instruction. In this embodiment, both the methods are implemented. The time-out time is one minute.

When the layout calculation is determined, the photographed image, layout coordinate determination values, and rotation/reversal determination values are stored in the nonvolatile memory device 1122 (hard disk in this embodiment) by a temporary storage section 1208. The photographed image is the image data input through the A/D converter 1107. The layout coordinate determination values represent the position of the irradiation field area relative to the film area. The rotation/reversal determination values are the rotation and reversal values of the image, which are determined by the display image rotation/reversal section 1204. The photographed image, layout coordinate determination values and the like are read out again for processing. This processing is performed as background processing.

Background processing is performed due to the following reason. Since the processing described above is performed using a reduced image mainly on the basis of logic calculation, the calculation time is relatively short. However, calculation for processing to be described below is done to, e.g., process the entire photographed image having a large size of 2,688×2,688 pixels, and takes a long time. During this processing, the user cannot start the next photographing operation. That is, when the processing is performed on the background, the operator can quickly start the next photographing cycle. Hence, processing from an extraction section 1209 to be described below is executed on the background.

The extraction section 1209 extracts a portion from the photographed imaging out from the nonvolatile memory device 1122 on the basis of the layout coordinate determination values read out from the nonvolatile memory device 1122. With this processing, the photographed image is trimmed in accordance with the layout coordinate determination values. As a result, a partial image of the irradiation field area is extracted from the photographed image.

The photographed image is appropriately processed by an image processing section 1210 to have appropriate contrast for diagnosis. After that, the photographed image is sent to a sensor position marking section 1211.

The sensor position marking section 1211 is used as a remedy when the designated rotation/reversal designation values have errors. For example, a remedy is required in the following case. Although the operator sets the PA (from the backside to the front) photographing mode, it may become apparent in actually determining the direction of the patient that the object need be photographed in the AP (from the front to the backside) photographing mode because of his/her condition of the disease. In such case, after the object is photographed, the operator may also forget to instruct the display image rotation/reversal section 1204 to reverse the image. Then, the image which must be reversed cannot be discriminated from the image normally photographed in the PA mode. This is because the film can be observed from both sides.

FIG. 26 is a view for explaining sensor position marking by the sensor position marking section. As shown in FIG. 26, after the image is extracted by the extraction section, the upper left position of the sensor is marked at the upper left corner of the image, which corresponds to the upper left portion of the sensor. Even when the image is rotated or reversed, the photographing direction of the image can be known. Since the sensor position is marked after extraction, the mark is not eliminated by extraction.

The marking information of the upper-left position of the sensor need not be always actually written in the image. Instead, information representing an image corner corresponding to the upper left portion of the sensor may be added to the header of the image data. In this case, especially when the final image is to be sent to a printer or a viewer, the receiving device must read and interpret this header information.

After sensor position marking, the image data is input to a rotation/reversal section 1212. The rotation/reversal section 1212 rotates and reverses the image in accordance with the stored rotation/reversal determination values. The processed image data is input to a reduction marking section 1213.

The reduction marking section 1213 marks to make it clear that the irradiation field area is reduced within the film to form a life-size image or less, as described with reference to FIG. 23. This reduction marking is necessary only when the output medium is a printer or a laser imager.

Many laser imagers have a function of printing a life-size image or less on the laser imager side without reducing the output image. In this embodiment, image reduction is not performed because it depends on such a laser imager.

This will be described in detail. The pixel size of the sensor of this embodiment is 160 μm. When an extracted image having a size of 2,048×2,560 pixels is to be sent to a laser imager with a size of 80 μm, an instruction for interpolating and enlarging the image to 2× is sent together. The laser imager interpolates and enlarges the image to 2×, so an image having a size of 4,096×5,120 pixels is output. This size is life size.

When the entire sensor area is explicitly selected by the operator for printing, the size is 2,688×2,688 pixels. In a printer with a size of 80 μm, which has a buffer area with a size of 4,096×5,120 pixels, the magnification of the image is limited by the magnification in the horizontal direction. That is, $$4096/2688=1.523$$

The image can be printed by interpolation and enlargement at the maximum magnification of about 1.523×. Hence, the image is transferred together with an instruction for the magnification of 1.523×. In terms of data, this processing is enlargement. However, when viewed from the operator, the output size is smaller than life size, and therefore, this processing is life-size reduction. FIG. 27 is a view showing an example of reduction marking. Referring to FIG. 27, reference numeral 1901 denotes reduction marking clearly representing that the image is reduced. After that, the image is externally output through an output section.

Figure 28:
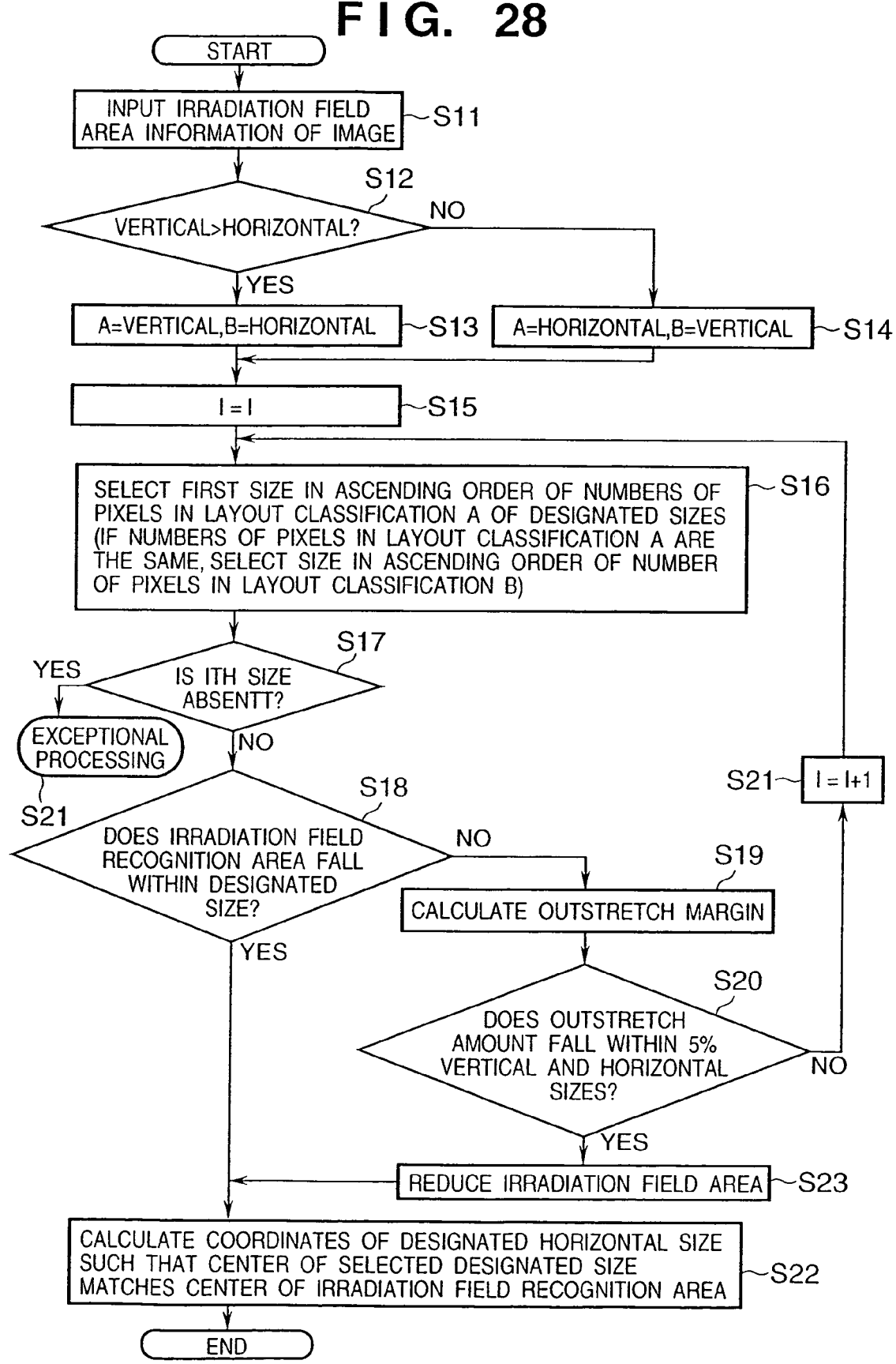
FIG. 28 is a flow chart showing processing by an irradiation field area layout calculation section.

Processing by the irradiation field area layout calculation section 1203 will be described next. FIG. 28 is a flow chart showing processing by the irradiation field area layout calculation section.

In step S11, irradiation field area information representing the irradiation field area of the photographed image is input from the irradiation field recognition section 1201. In step S12, the vertical length of the recognized irradiation field area is compared with the horizontal length. If the vertical length is larger, A is the vertical direction, and B is the horizontal direction (step S13). If the horizontal length is larger, A is the horizontal direction, and B is the vertical direction (step S14).

In step S15, a variable I is initialized. This variable I is used to check a table which records designated sizes in advance. In this embodiment, the table shown in FIG. 22 is used. This table can be registered by the operator in advance as initial setting. That is, the operator can register desired designated sizes in advance.

In step S16, from the layout classification A in the table shown in FIG. 22 (when the irradiation field area is vertically elongated, the layout classification "vertical" is selected in FIG. 22), the Ith size counted from a small number of pixels in the A direction is selected (at the first time processing of this step, the first size is selected) If the number of pixels in the A direction is the same, the number of pixels is selected in ascending order in the B direction. The vertical and horizontal sizes are used as indices in the table, and sizes are arranged in descending order in each index. For the same size, when the layout classification is "vertical", sizes are arranged in the order of horizontal sizes. When the layout classification is "horizontal", the sizes are arranged in the order of vertical sizes (For example, when A is the vertical direction (layout classification is "vertical"), sizes are searched in ascending order of vertical sizes. The smallest size is "¼-size portrait). The second smallest size is "large-size" and "half-size portrait"). However, when the number of pixels in the horizontal direction is taken into consideration, the second smallest size is "large-size").

In step S17, it is determined whether the Ith size is selected in step S16. In processing of step S16 and steps S18 to 21 to be described below, the variable I is incremented by one until an appropriate size is acquired. If the Ith size is not present any more, this means an appropriate size cannot be selected. Hence, if it is determined in step S17 that the Ith designated size is not present, exceptional processing is performed. For example, in the table shown in FIG. 22, no fourth smallest size is present in the vertical direction. For this reason, when I=4, the flow advances to exceptional processing. One of the three measures described with reference to FIGS. 23 to 25 is performed as exceptional processing.

When the Ith designated size is selected in step S16, the flow advances from step S17 to step S18. In step S18, it is determined whether the irradiation field area input in step S11 falls within the selected designated size. If YES in step S18, the flow advances to step S22 to determine the coordinates of the designated size (obtain layout coordinate determination) such that the center of the selected designated size matches the center of the recognized irradiation field area, and processing is ended.

Figure 29:
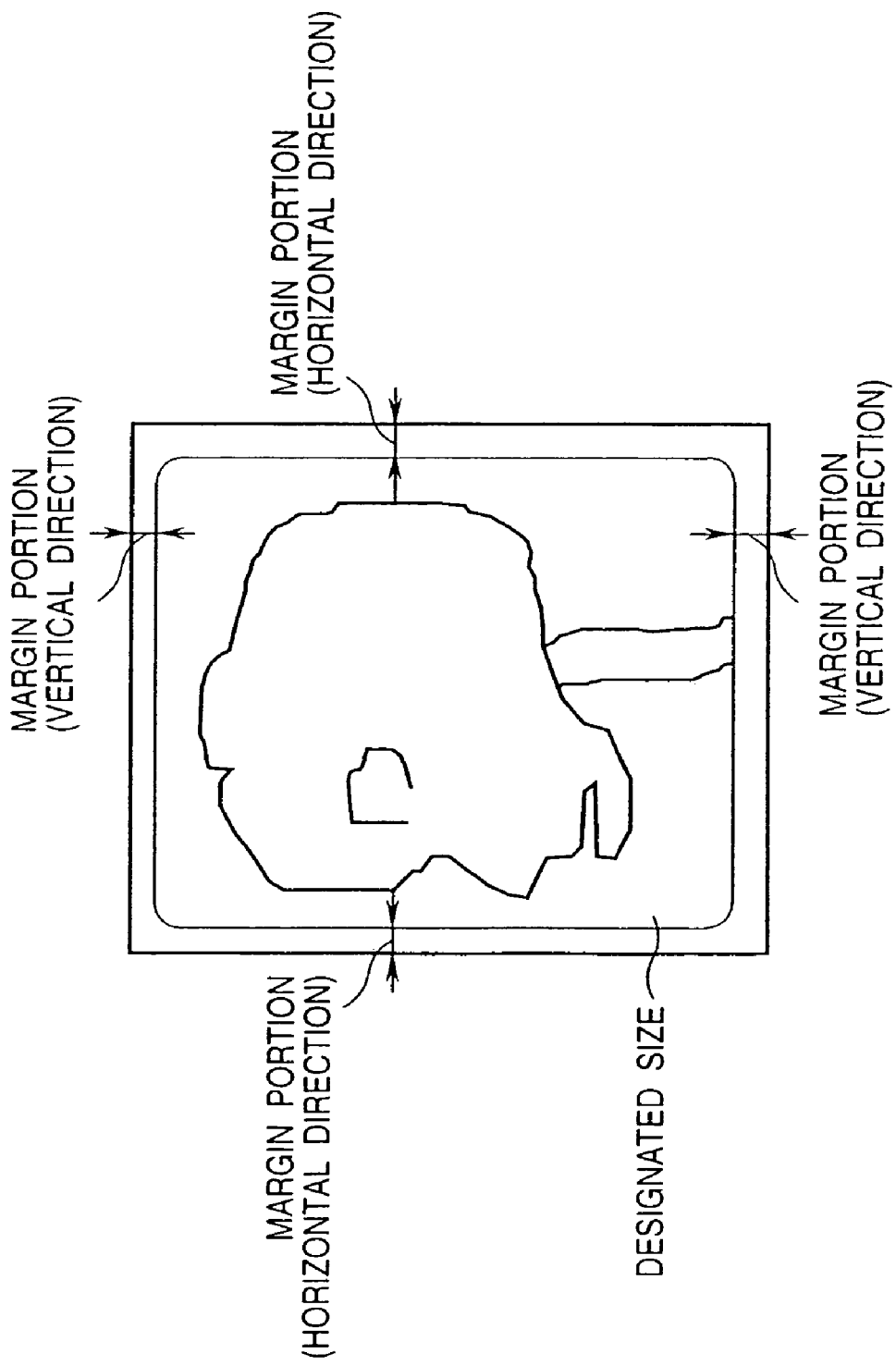
FIG. 29 is a view for explaining outstretch margin calculation of the fourth embodiment.

If NO in step S18, the flow advances to step S19 to calculate the outstretch margin. FIG. 29 is a view for explaining outstretch margin calculation of this embodiment. Generally, the irradiation field boundary of the recognized irradiation field is vague. The area effective for diagnosis is near the central portion of the image. For this reason, even when a small portion of the vicinity of the irradiation field area is excluded, the area effective for diagnosis is not excluded. As shown in FIG. 29, as long as the vertical and horizontal outstretch portions (margins) with respect to the film size (designated size) fall within predetermined ranges, respectively, it is determined that the irradiation field area can be matched with the horizontal or vertical size of the designated size. This also applies to a case wherein the irradiation field area stretches out only in the horizontal direction or only in the vertical direction. In this embodiment, in step S19, the size of the outstretch portion is calculated. In step S20, it is determined whether that size falls within 5% the film length in the outstretch direction (the vertical outstretch portion is compared with the vertical film length, and the horizontal outstretch portion is compared with the horizontal film length). If YES in step S20, the flow advances to step S23 to make the irradiation field area smaller than the irradiation field area calculation result such that the irradiation field area falls within the designated size. The flow advances to step S22 to determine the layout coordinates.

If NO in step S20, the flow advances to step S21 to increment the variable I to check the next designated size, and the flow returns to step S16.

In the above way, the irradiation field area layout calculation section 1203 selects an appropriate size for output on the basis of the recognized irradiation field area, and determines the layout position of the irradiation field area in the selected designated size.

Figure 30A:
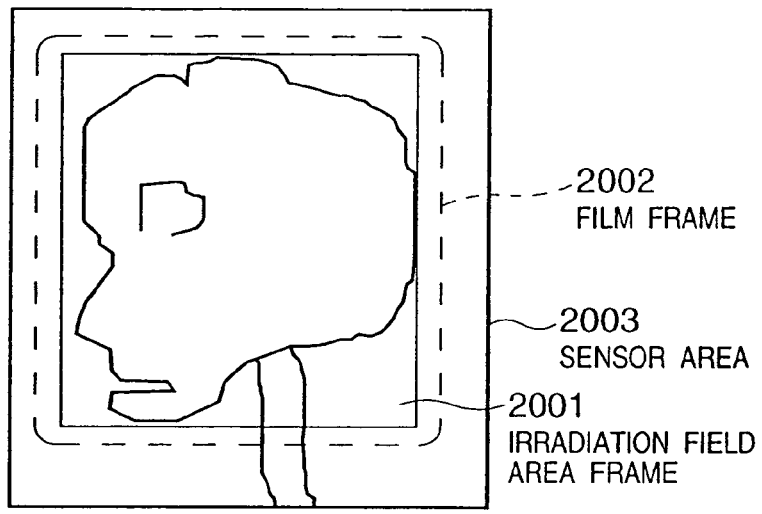
FIGS. 30A to 30C are views for explaining a display scheme of a display section 1206.
Figure 30B:
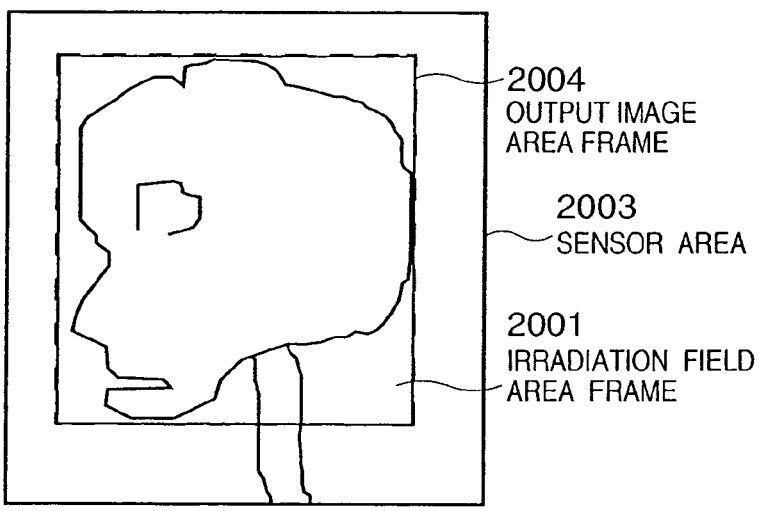
Figure 30C:
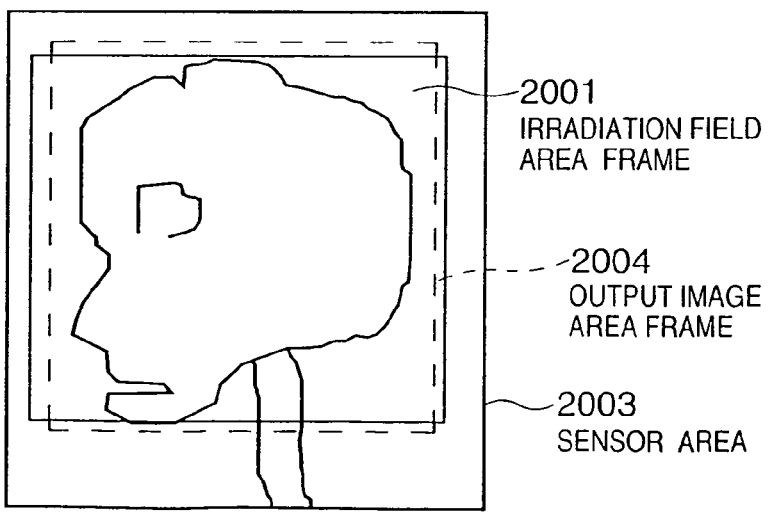

FIGS. 30A to 30C are views for explaining the display method on the display section 1206. FIG. 30A shows a state wherein the reduced images of an irradiation field area frame 2001, film frame 2002, and sensor area (entire image area) 2003 are overlaid and displayed on the basis of the calculated layout. In FIGS. 30B and 30C, the reduced images of the irradiation field area, frame 2001, sensor area 2003, and an output image area frame 2004 are overlaid and displayed. The output image area frame 2004 represents the output image area determined by irradiation field area layout calculation described with reference to FIG. 28. No film frame is displayed in FIGS. 30B and 30C. In the system of this embodiment, one of the display forms shown in FIGS. 30A to 30C can be arbitrarily selected.

As has been described above, according to the fourth embodiment of the present invention, the effective portion of an image can be output with an appropriate size using a commercially available film having a predetermined size or a commercially available image viewer having a predetermined maximum allowable size. Hence, an image can be formed on an existing medium or viewer without damaging the information. As a consequence, since no custom-made film, printer, or image viewer need be used, the cost effect for users becomes large.

In this embodiment, for easier implementation and descriptive convenience, most processing operations are realized by software. However, they can also be realized by hardware without departing from the scope or spirit of the present invention.

The present invention may be applied to a system constituted by a plurality of devices (e.g., a host computer, an interface device, a reader, a printer, and the like) or an apparatus comprising a single device (e.g., a copying machine, a facsimile apparatus, or the like).

The object of the present invention is realized even by supplying a storage medium storing software program codes for realizing the functions of the above-described embodiments to a system or an apparatus, and causing the computer (or a CPU or an MPU) of the system or the apparatus to read out and execute the program codes stored in the storage medium.

In this case, the program codes read out from the storage medium realize the functions of the above-described embodiments by themselves, and the storage medium storing the program codes constitutes the present invention.

As a storage medium for supplying the program codes, a floppy disk, a hard disk, an optical disk, a magneto optical disk, a CD-ROM, a CD-R, a magnetic tape, a nonvolatile memory card, a ROM, or the like can be used.

The functions of the above-described embodiments are realized not only when the readout program codes are executed by the computer but also when the OS (Operating System) running on the computer performs part or all of actual processing on the basis of the instructions of the program codes.

The functions of the above-described embodiments are also realized when the program codes read out from the storage medium are written in the memory of a function expansion board inserted into the computer or a function expansion unit connected to the computer, and the CPU of the function expansion board or function expansion unit performs part or all of actual processing on the basis of the instructions of the program codes.

As many apparently widely different embodiments of the present invention can be made without departing from the spirit and scope thereof, it is to be understood that the invention is not limited to the specific embodiments thereof except as defined in the appended claims.

What is claimed is:

1. An image processing apparatus comprising:
   acquisition means for specifying a to-be-output area of an input image represented by image data as an output image and acquiring a site of the output image;
   selection means for selecting, on the basis of the size of the output image acquired by said acquisition means, one image output size from a plurality of image output sizes set in advance;
   layout determination means for determining a layout state of the output image in an output area having the image output size selected by said selection means;
   selection changing means for making said selection means select another image output size different from the image output size selected by said selection means if an extending length of an outstretch margin exceeds a corresponding length of the output area indicated by the layout state by more than a predetermined amount, wherein the outstretch margin is a portion of the output image extending beyond the output area in either a horizontal or vertical direction; and
   output area changing means for reducing the to-be-output area so that the output image fits within the output area if the extending length of the outstretch margin does not exceed the corresponding length of the output area by more than the predetermined amount.

2. The apparatus according to claim 1, further comprising display means for displaying layout information on the basis of the layout state determined by said layout determination means, wherein said display means reduces the output area and the output image and displays the output image in the layout state determined by said layout determination means.

3. The apparatus according to claim 1, further comprising display means for displaying layout information on the basis of the layout state determined by said layout determination means, wherein said display means overlays, in accordance with the layout state, an image obtained by reducing an image representing the output area on an image obtained by reducing the input image represented by the image data, and displays the resulting layout information.

4. The apparatus according to claim 1, further comprising:
display means for displaying layout information on the basis of the layout state determined by said layout determination means;
change means for changing the layout state of the output image in the output area in accordance wit an instruction for changing the layout state information displayed by said display means; and
output means for outputting the output image to an output medium having the output area on the basis of a final layout state determined by said layout determination means and said change means.

5. The apparatus according to claim 1, wherein said selection means selects an image output size having a minimum residual area, within which the entire output image falls.

6. The apparatus according to claim 5, wherein said selection means selects an image output size assuming that the entire output image falls within the image output size as long as the outstretch margin falls within a predetermined range, and removes the outstretch margin from the output image.

7. The apparatus according to claim 1, further comprising reduction means for, when no appropriate image output size is obtained by said selection means, reducing the output image such that the output image falls within a predetermined output area.

8. The apparatus according to claim 7, further comprising:
display means for displaying layout information on the basis of the layout state determined by said layout determination means;
change means for changing the layout state of the output image in the output area in accordance with an instruction for changing the layout state information displayed by said display means;
output means for outputting the output image to an output medium having the output area on the basis of a final layout state determined by said layout determination means and said change means; and
addition means for, when the output image is reduced by said reduction means, adding one of a symbol and a character representing reduction to the output image.

9. The apparatus according to claim 1, further comprising deletion means for, when no appropriate image output size is obtained by said selection means, deleting an outstretch portion of the output image from a predetermined output area.

10. The apparatus according to claim 1, further comprising extraction means for, when no appropriate image output size is obtained by said selection means, displaying the output image overlaid on a predetermined output area and extracting a desired area from the output image by a user's operation.

11. The apparatus according to claim 1, further comprising display means for displaying layout information on the basis of the layout state determined by said layout determination means, wherein said display means displays the entire input image represented by the image data, a range of the output image, and the output area in an identifiable state.

12. The apparatus according to claim 1, further comprising display means for displaying layout information on the basis of the layout state determined by said layout determination means, wherein said display means displays the entire input image represented by the image data, the to-be-output area specified by said acquisition means, and the output area to be actually output in an identifiable state.

13. The apparatus according to claim 1, wherein the image data represents an X-ray digital image obtained by X-ray irradiation, and
the output image specified by said acquisition means is an image of an area specified by recognizing an irradiation field in the X-ray digital image.

14. The apparatus according to claim 13, wherein the plurality of output sizes correspond to a plurality of film sizes, respectively, and
said apparatus further comprises:
display means for displaying layout information on the basis of the layout state determined by said layout determination means;
change means for changing the layout state of the output image in the output area in accordance with an instruction for changing the layout state information displayed by said display means; and
output means for extracting the output image and outputting the output image to a film having the output area on the basis of a final layout state determined by said layout determination means and said change means.

15. A computer readable storage medium which stores a control program for causing a computer to control an output image size, wherein the control program comprises:
a code of an acquisition step of specifying a to-be-output area of an input image represented by image data as an output image and acquiring a size of the output image;
a code of a selection step of selecting, on the basis of the size of the output image acquired in the acquisition step, one image output size from a plurality of image output sizes set in advance;
a code of a layout determination step of determining a layout state of the output image in an output area having the image output size selected in the selection step;
a code of a selection changing step of making said selection step select another image output size different from the image output size selected by said selection step if an extending length of an outstretch margin exceeds a corresponding length of the output area indicated by the layout state by more than a predetermined amount, wherein the outstretch margin is a portion of the output image extending beyond the output area in either a horizontal or vertical direction; and
a code of an output area changing step of reducing the to-be-output area so that the output image fits within the output area if the extending length of the outstretch margin does not exceed the corresponding length of the output area by more than the predetermined amount.

* * * * *